United States Patent
Gaster et al.

(10) Patent No.: US 9,506,919 B2
(45) Date of Patent: Nov. 29, 2016

(54) METHODS AND DEVICES FOR DETECTING THE PRESENCE OF AN ANALYTE IN A SAMPLE

(75) Inventors: Richard Samuel Gaster, Los Altos, CA (US); Drew Hall, Stanford, CA (US); Shan X. Wang, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1204 days.

(21) Appl. No.: 12/759,584

(22) Filed: Apr. 13, 2010

(65) Prior Publication Data

US 2011/0027901 A1    Feb. 3, 2011

Related U.S. Application Data

(60) Provisional application No. 61/168,922, filed on Apr. 13, 2009.

(51) Int. Cl.
*G01N 33/543* (2006.01)
*G01N 27/74* (2006.01)
*G01N 33/574* (2006.01)
(Continued)

(52) U.S. Cl.
CPC ...... *G01N 33/54373* (2013.01); *G01N 27/745* (2013.01); *G01N 33/574* (2013.01); *G01N 21/553* (2013.01); *G01N 21/6428* (2013.01);
(Continued)

(58) Field of Classification Search
CPC ............ G01N 27/745; G01N 33/54373; G01N 33/574; G01N 21/553; G01N 21/6428; G01N 21/658; G01N 2201/0221; Y10T 436/25
USPC ................. 436/518, 526
See application file for complete search history.

(56) References Cited

U.S. PATENT DOCUMENTS 5,485,277 A *  1/1996 Foster .................. 356/445
5,981,297 A   11/1999 Baselt
(Continued)

FOREIGN PATENT DOCUMENTS

EP    2034324    3/2009
JP    2004-167032 A    6/2004
(Continued)

OTHER PUBLICATIONS

Gaster; et al., "Matrix-insensitive protein assays push the limits of biosensors in medicine", Nature Medicine (2009), pp. 1-7.
(Continued)

*Primary Examiner* — Mark Shibuya
*Assistant Examiner* — Pensee Do
(74) *Attorney, Agent, or Firm* — Rudy J. Ng; Bret E. Field; Bozicevic, Field & Francis LLP

(57) ABSTRACT

Sensor assay methods for detecting the presence of an analyte in a sample are provided. Aspects of the methods include providing a sensor, e.g., a proximity sensor, in contact with an assay composition that includes a sample and a proximity label. Next, a capture probe configured to bind to the proximity label and the analyte is introduced into the assay composition to produce a labeled analyte. Following capture probe introduction, a signal is obtained from the sensor to detect the presence of the labeled analyte in the sample. Also provided are sensor devices, including handheld devices, and kits that find use in practicing the subject methods.

15 Claims, 20 Drawing Sheets

(51) Int. Cl.
  *G01N 21/552* (2014.01)
  *G01N 21/64* (2006.01)
  *G01N 21/65* (2006.01)

(52) U.S. Cl.
  CPC ..... *G01N 21/658* (2013.01); *G01N 2201/0221* (2013.01); *Y10T 436/25* (2015.01)

(56) References Cited

U.S. PATENT DOCUMENTS

| | | |
|---|---|---|
| 6,057,167 A | 5/2000 | Shieh et al. |
| 6,670,115 B1 | 12/2003 | Zhang |
| 6,743,639 B1 | 6/2004 | Tondra et al. |
| 7,048,890 B2 | 5/2006 | Coehoorn et al. |
| 7,238,486 B2 | 7/2007 | Pourmand et al. |
| 7,373,255 B2 | 5/2008 | Karlsson et al. |
| 7,419,639 B2 | 9/2008 | Osterfeld et al. |
| 7,501,253 B2 | 3/2009 | Pourmand et al. |
| 7,504,262 B2 | 3/2009 | Fox |
| 7,615,382 B2 | 11/2009 | Wang et al. |
| 7,682,838 B2 | 3/2010 | Wang et al. |
| 7,766,993 B2 | 8/2010 | Sun et al. |
| 7,906,345 B2 | 3/2011 | Wang et al. |
| 7,939,338 B2 | 5/2011 | Wang et al. |
| 7,977,111 B2 | 7/2011 | Shi et al. |
| 7,989,396 B2 | 8/2011 | Yu et al. |
| 2002/0000398 A1* | 1/2002 | Skold ............ 209/214 |
| 2002/0081617 A1 | 6/2002 | Buranda et al. |
| 2005/0014179 A1 | 1/2005 | Karlsson et al. |
| 2005/0019842 A1* | 1/2005 | Prober et al. ............ 435/7.9 |
| 2005/0100930 A1 | 5/2005 | Wang et al. |
| 2005/0131650 A1 | 6/2005 | Andersson et al. |
| 2006/0286685 A1* | 12/2006 | Miller et al. ............ 436/526 |
| 2007/0207553 A1 | 9/2007 | Fox |
| 2007/0264159 A1 | 11/2007 | Graham et al. |
| 2008/0036450 A1 | 2/2008 | Kahlman et al. |
| 2008/0054896 A1 | 3/2008 | Kahlman et al. |
| 2008/0311598 A1 | 12/2008 | Vossenaar et al. |
| 2008/0318339 A1 | 12/2008 | Vossenaar et al. |
| 2009/0104707 A1* | 4/2009 | Wang ............ G01N 33/54326 436/86 |
| 2009/0181464 A1 | 7/2009 | De Theije et al. |
| 2010/0148768 A1 | 6/2010 | Schwarz |
| 2010/0188075 A1 | 7/2010 | Litvinov et al. |
| 2010/0248283 A1* | 9/2010 | Xiao et al. ............ 435/29 |
| 2010/0289483 A1 | 11/2010 | Immink et al. |
| 2011/0151429 A1 | 6/2011 | Haam et al. |
| 2011/0223612 A1 | 9/2011 | Wang et al. |

FOREIGN PATENT DOCUMENTS

| | | | |
|---|---|---|---|
| JP | 2006184250 | 7/2006 | |
| JP | 2008268186 | 11/2008 | |
| JP | 2008-546995 | 12/2008 | |
| JP | 2009-531023 | 9/2009 | |
| WO | 03/031977 | 4/2003 | |
| WO | 03/081202 | 10/2003 | |
| WO | 2006/059270 | 6/2006 | |
| WO | 2006/075612 A1 | 7/2006 | |
| WO | WO2007132374 A1 * | 11/2007 | ........ G01N 33/543 |
| WO | 2009/125825 | 10/2009 | |

OTHER PUBLICATIONS

Osterfeld; et al., "Multiplex protein assays based on real-time magnetic nanotag sensing", PNAS (2008), 105(52):20637-20640.

Xu; et al., "Giant Magnetoresistive Biochip for DNA Detection and HPV Genotyping", Biosens Bioelectron (2008), 24(1):99-103.

De Boer; et al., "An integrated and sensitive detection platform for magneto-resistive biosensors", Biosensors and Bioelectronics (2007), 22:2366-2370.

Mulvaney; et al., "Attomolar protein detection in complex sample matrices with semi-homogeneous fluidic force discrimination assays", Biosensors and Bioelectronics (2009), 24:1109-15.

Martin; et al., "Challenges and trends in the development of a magnetoresistive biochip portable platform", Journal of Magnetism and Magnetic Materials (2010), 322:1655-1663.

Baselt et al. "A biosensor based on magnetoresistance technology", Biosensors & Bioelectronics, vol. 13, Issues 7-8, Oct. 1998, pp. 731-739.

* cited by examiner

METHODS AND DEVICES FOR DETECTING THE PRESENCE OF AN ANALYTE IN A SAMPLE

CROSS-REFERENCE TO RELATED APPLICATIONS

Pursuant to 35 U.S.C. §119 (e), this application claims priority to the filing date of U.S. Provisional Patent Application Ser. No. 61/168,922 filed on Apr. 13, 2009; the disclosure of which application is herein incorporated by reference.

ACKNOWLEDGMENT OF GOVERNMENT SUPPORT

This invention was made with Government support under Grant Nos. CA119367 from the National Institutes of Health, HDTRA1-07-1-0030 awarded by Defense Threat Reduction Agency, and ECCS-0801385 from the National Science Foundation. The Government has certain rights in this invention.

INTRODUCTION

Nanotechnology is well-suited for rapid and sensitive analyte, e.g., protein, detection due to its ability to transduce molecular events into signals measurable by macroscopic instrumentation. Driven by the need for highly sensitive and specific analyte detection, researchers have begun to shift to the nanoscale for accurate detection. The vast majority of analyte detection platforms, however, require a series of time intensive and laborious washing steps prior to detection. In the laboratory setting, such a requirement is simple to implement. However, for rapid diagnostics at the bedside, in third-world countries, or, for over the counter general consumer use, this requirement is impractical.

For example, in third world countries, access to medical diagnostic laboratories and well trained technicians is limited. As a result, the majority of diagnoses in these regions are based upon patient signs and symptoms.

While this method of patient care is suitable in straightforward situations such as diagnosing the flu, the vast majority of illnesses cannot be determined by simple observation. In contrast, in the developed world, medical decision-making is increasingly based on molecular testing where quantitative detection of disease-specific analytes in serum and other bodily fluids has become the basis behind virtually any therapy.

SUMMARY

Sensor assay methods for detecting the presence of an analyte in a sample are provided. Aspects of the methods include providing a sensor, such as a proximity sensor, in contact with an assay composition that includes a sample and a proximity label. Next, a capture probe configured to bind to the proximity label and the analyte is introduced into the assay composition to produce a labeled analyte. Following capture probe introduction, a signal is obtained from the sensor to detect the presence of the labeled analyte in the sample. Also provided are proximity sensor devices, including hand-held devices, and kits that find use in practicing the subject methods.

BRIEF DESCRIPTION OF THE FIGURES

FIG. 7($b$) shows a photograph of a planar electromagnet and magnetic flux guides according to embodiments of the present disclosure.

FIG. 16($b$) shows a graph of the change in magnetoresistance normalized to the initial magnetoresistance presented in parts per million (ppm) for each proximity sensor in the array.

DETAILED DESCRIPTION

Figure 1:
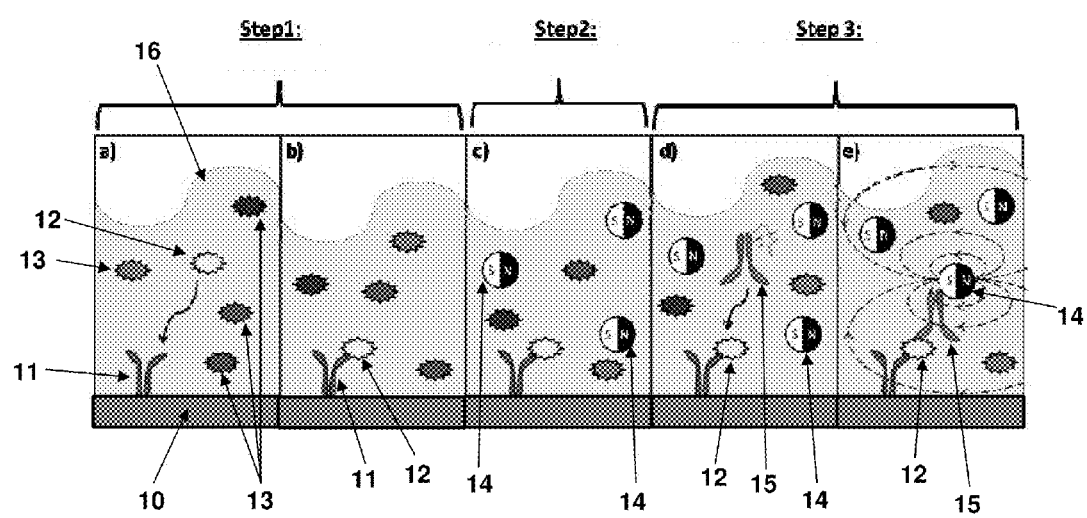
FIG. 1 shows an illustration of a method of detecting the presence of an analyte in a sample according to embodiments of the present disclosure.

Sensor assay methods for detecting the presence of an analyte in a sample are provided. Aspects of the methods include providing a sensor (e.g., a proximity sensor) in contact with an assay composition that includes a sample and a proximity label. Next, a capture probe configured to bind to the proximity label and the analyte is introduced into the assay composition to produce a labeled analyte. Following capture probe introduction, a signal is obtained from the sensor to detect the presence of the labeled analyte in the sample. Also provided are sensor devices, including handheld devices, and kits that find use in practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, aspects of embodiments of the methods will be described first in greater detail. Next, embodiments of systems and kits that may be used in practicing the subject methods are reviewed.

Methods

As summarized above, embodiments of the methods are directed to determining whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular structure, sequence, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

In some instances, the methods are wash-free methods of determining the presence of one or more analytes in a sample. By "wash-free" is meant that no washing step is performed following reagent and/or sample contact with a sensor surface. As such, no step is performed during the assays of these embodiments in which unbound reagent or unbound sample is removed from the sensor surface. Accordingly, while the methods may include sequential contact of one or more distinct reagents and/or samples to a sensor surface, at no point during the assays is the sample surface contacted with a fluid in a manner that removes unbound reagent or sample from the sensor surface. For example, in certain embodiments, no washing step is performed following contact of the sensor surface with a sample. In some cases, the method does not include a washing step following contact of the sensor with a proximity label. In certain instances, no washing step is performed following contact of the sensor surface with a capture probe.

As summarized above, aspects of the methods include first providing a sensor, such as a proximity sensor in contact with an assay composition that includes a sample and a proximity label. Next, a capture probe configured to bind to the proximity label and the analyte is introduced into the assay composition. Following capture probe introduction, a signal is obtained from the sensor to detect the presence of the analyte in the sample. Each of these steps will now be described in greater detail.

Producing a Sensor in Contact with an Assay Composition that Includes a Sample and a Proximity Label Aspects of the methods include producing a sensor that is in contact with a sample and a proximity label. As such, the methods include producing a device in which a sensor is contacted with an assay composition that includes a sample and a proximity label.

Sample

As described above, assay compositions that may be assayed in the subject methods include a sample and a proximity label. Samples that may be assayed in the subject methods may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure.

In certain embodiments, the samples of interest are biological samples, such as, but not limited to, urine, blood, serum, plasma, saliva, perspiration, feces, cheek swabs, cerebrospinal fluid, cell lysate samples, and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In some instances, the samples of interest are water, food or soil samples.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

Proximity Labels

As described above, assay compositions that may be assayed in the subject methods include a sample and a proximity label. Proximity labels are labeling moieties that are detectable by a sensor, such as a proximity sensor, when the proximity label is positioned near the sensor. While the distance between the proximity label and sensor surface during detection may vary depending on the nature of the specific proximity label and sensor surface, in some instances this distance ranges from 1 nm to 200 nm from the surface of the sensor, such as from 5 nm to 150 nm, including from 5 nm to 100 nm. In certain embodiments, the proximity labels are detectable labels that are configured to specifically bind to an analyte of interest. The terms "specific binding," "specifically bind," and the like, refer to the ability of a first binding molecule or moiety (e.g., a target-specific binding moiety) to preferentially bind directly to a second binding molecule or moiety (e.g., a target molecule) relative to other molecules or moieties in a solution or reaction mixture. In certain embodiments, the affinity between a first binding molecule or moiety and a second binding molecule or moiety when they are specifically bound to each other in a binding complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

Binding of the proximity label to the analyte of interest allows the analyte of interest to be detected by a sensor, such as a proximity sensor, when the analyte of interest, and thus the bound proximity label, is positioned near the sensor. In some cases, the proximity labels are configured to bind directly to an analyte of interest. In other cases, the proximity labels are configured to indirectly bind to an analyte of interest. For instance, a proximity label may be configured to specifically bind to a capture probe, and the capture probe may be configured to specifically bind to the analyte of interest. Thus, binding of the proximity label and the analyte of interest to the capture probe indirectly binds the proximity label to the analyte of interest, e.g., to produce a labeled analyte. In some instances, the binding of the proximity label and analyte to the capture probe is simultaneous.

In certain embodiments, the proximity label is functionalized with one member of a binding pair. By "binding pair" or "specific binding pair" is meant two complementary binding molecules or moieties that specifically bind to each other in a binding complex. For example, a proximity label may be functionalized with a first member of a binding pair and an analyte of interest may be functionalized with a second member of a binding pair. Thus, contacting the first and second members of the binding pair may form a binding complex between the proximity label and the analyte of interest. In other cases, a proximity label is functionalized with a first member of a binding pair and a capture probe is functionalized with a second member of a binding pair. Thus, contacting the first and second members of the binding pair may form a binding complex between the proximity label and the capture probe. As described above, in some cases, the capture probe is configured to specifically bind to an analyte of interest. As such, the proximity label may be indirectly bound to the analyte of interest through the binding complex formed between the proximity label and the capture probe. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the proximity label is functionalized with streptavidin and the capture probe is functionalized with biotin. As such, the proximity label may specifically bind to the capture probe through the specific binding interaction between streptavidin and biotin. Other types of binding interactions are also possible. For example, the proximity label may be functionalized with biotin and the capture probe may be functionalized with streptavidin. Alternatively, the proximity label and the capture probe may be functionalized with complementary members of other specific binding pairs, as described above.

In some instances, the proximity label is stably associated with one member of a binding pair. By "stably associated" is meant that the proximity label and the member of the binding pair maintain their position relative to each other in space under the conditions of use, e.g., under the assay conditions. As such, the proximity label and the member of the binding pair can be non-covalently or covalently stably associated with each other. Examples of non-covalent association include non-specific adsorption, binding based on electrostatic (e.g., ion-ion pair interactions), hydrophobic interactions, hydrogen bonding interactions, and the like. Examples of covalent binding include covalent bonds formed between the member of the binding pair and a functional group present on the surface of the proximity label.

In certain embodiments, the proximity labels are colloidal. The terms "colloid" or "colloidal" refer to a mixture in which one substance is dispersed throughout another substance. Colloids include two phases, a dispersed phase and a continuous phase. In some instances, colloidal proximity labels remain dispersed in solution and do not precipitate or settle out of solution. Colloidal proximity labels that remain dispersed in solution may facilitate a minimization in background signals and non-specific interaction of the proximity labels with the proximity sensor. For example, the methods may include contacting a proximity sensor with an assay composition that includes a sample and a proximity label, such that an analyte of interest in the sample is bound to the surface of the proximity sensor. Because the colloidal proximity labels remain dispersed in solution, the proximity labels are not positioned near enough to the proximity sensor to induce a detectable signal in the proximity sensor, which facilitates a minimization in background signals. In some cases, specific binding of the proximity labels to the surface-bound analyte positions the proximity label near the proximity sensor, such that a detectable signal is induced in the proximity sensor.

Proximity labels that may be employed in various methods (e.g., as described herein) may vary, and include any type of label that induces a detectable signal in a proximity sensor when the proximity label is positioned near the surface of the proximity sensor. For example, proximity labels may include, but are not limited to, magnetic labels, optical labels (e.g., surface enhanced Raman scattering (SERS) labels), fluorescent labels, and the like. Each of these types of proximity labels are discussed in more detail below.

Magnetic Labels

In certain embodiments, the proximity label is a magnetic label. Magnetic labels are labeling moieties that, when sufficiently associated with a magnetic proximity sensor, are detectable by the magnetic proximity sensor and cause the magnetic proximity sensor to output a signal. For example, the presence of a magnetic label near the surface of a magnetic proximity sensor may induce a detectable change in the magnetic proximity sensor, such as, but not limited to, a change in resistance, conductance, inductance, impedance, etc. In some cases, the presence of a magnetic label near the surface of a magnetic proximity sensor induces a detectable change in the resistance of the magnetic proximity sensor. Magnetic labels of interest may be sufficiently associated with a magnetic proximity sensor if the distance between the center of the magnetic label and the surface of the sensor is 200 nm or less, such as 150 nm or less, including 100 nm or less.

In certain instances, the magnetic labels include one or more materials selected from paramagnetic, superparamagnetic, ferromagnetic, ferromagnetic, anti-ferromagnetic materials, combinations thereof, and the like. For example, the magnetic labels may include superparamagnetic materials. In certain embodiments, the magnetic labels are configured to be nonmagnetic in the absence of an external magnetic field. By "nonmagnetic" is meant that the magnetization of a magnetic labels is zero or averages to zero over a certain period of time. In some cases, the magnetic label may be nonmagnetic due to random flipping of the magnetization of the magnetic label over time. Magnetic labels that are configured to be nonmagnetic in the absence of an external magnetic field may facilitate the dispersion of the magnetic labels in solution because nonmagnetic labels do not normally agglomerate in the absence of an external magnetic field. In certain embodiments, the magnetic labels include superparamagnetic materials or synthetic antiferromagnetic materials. For instance, the magnetic labels may include two or more layers of antiferromagnetically-coupled ferromagnets.

In certain embodiments, the magnetic labels are high moment magnetic labels. The magnetic moment of a magnetic label is a measure of its tendency to align with an external magnetic field. By "high moment" is meant that the magnetic labels have a greater tendency to align with an external magnetic field. Magnetic labels with a high magnetic moment may facilitate the detection of the presence of the magnetic labels near the surface of the proximity sensor because it is easier to induce the magnetization of the magnetic labels with an external magnetic field.

In certain embodiments, the magnetic labels include, but are not limited to, Co, Co alloys, ferrites, cobalt nitride, cobalt oxide, Co—Pd, Co—Pt, iron, iron oxides, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. Examples of high moment magnetic labels include, but are not limited to, Co, Fe or CoFe nanocrystals, which may be superparamagnetic at room temperature. In some embodiments, the surface of the magnetic label is modified. In certain instances, the magnetic labels may be coated with a layer configured to facilitate stable association of the magnetic label with one member of a binding pair, as described above. For example, the magnetic label may be coated with a layer of gold, a layer of poly-L-lysine modified glass, dextran, and the like. In certain embodiments, the magnetic labels include one or more iron oxide cores imbedded in a dextran polymer. Additionally, the surface of the magnetic label may be modified with one or more surfactants. In some cases, the surfactants facilitate an increase in the water solubility of the magnetic labels. In certain embodiments, the surface of the magnetic labels are modified with a passivation layer. The passivation layer may facilitate the chemical stability of the magnetic labels in the assay conditions. For example, the magnetic labels may be coated with a passivation layer that includes gold, iron oxide, polymers (e.g., polymethylmethacrylate films), and the like.

In certain embodiments, the magnetic labels have a spherical shape. Alternatively, the magnetic labels can be disks, rods, coils, or fibers. In some cases, the size of the magnetic labels is such that the magnetic labels do not interfere with the binding interaction of interest. For example, the magnetic labels may be comparable to the size of the analyte and the capture probe, such that the magnetic labels do not interfere with the binding of the capture probe to the analyte. In some cases, the magnetic labels are magnetic nanoparticles. In some embodiments, the average diameter of the magnetic labels is from 5 nm to 250 nm, such as from 5 nm to 150 nm, including from 10 nm to 100 nm, for example from 25 nm to 75 nm. For example, magnetic labels having an average diameter of 5 nm, 10 nm, 20 nm, 25 nm, 30 nm, 35 nm, 40 nm, 45 nm, 50 nm, 55 nm, 60 nm, 70 nm, 80 nm, 90 nm, or 100 nm, as well as magnetic labels having average diameters in ranges between any two of these values, may be used with the subject methods. In some instances, the magnetic labels have an average diameter of 50 nm.

Magnetic labels and their conjugation to biomolecules are further described in U.S. Ser. No. 12/234,506, filed Sep. 19, 2008, and entitled "Analyte Detection with Magnetic Sensors", the disclosure of which is hereby incorporated by reference in its entirety.

Optical Labels

In certain embodiments, the proximity label is an optical label. Optical labels are labeling moieties that are detectable using optical label detection techniques, such as, but not limited to, Raman spectroscopy, surface enhanced Raman spectroscopy (SERS), surface plasmon resonance, and the like.

In some cases, the optical label includes a surface enhanced Raman scattering (SERS) label. SERS labels are labeling moieties that are detectable when sufficiently associated with a proximity sensor (e.g., a surface plasmon resonance (SPR) detector). For example, the presence of a SERS label near the surface of a SPR detector may induce a detectable enhancement of Raman scattering by the SERS label. SERS labels of interest may be sufficiently associated with a proximity sensor if the distance between the center of the SERS label and the surface of the sensor is 200 nm or less, such as 150 nm or less, including 100 nm or less.

In certain embodiments, the SERS labels include a core, a layer of Raman reporter molecules, and a coating. The core can include materials such as, but not limited to, metals. The core can be a metallic core. For example, the core can include materials such as, but not limited to, gold, silver, platinum, copper, aluminum, transition metals (e.g., Zn, Ni, Cd, and the like), semiconductors (e.g., CdSe, CdS, InAs, and the like), and combinations thereof. In some instances, the core is a gold core.

The layer of Raman reporter molecules can include molecules such as, but not limited to, organic dye molecules having an isothiocyanate group (hereinafter "isothiocyanate dyes"), organic dye molecules having two or more sulfur atoms (hereinafter "multi-sulfur organic dyes"), organic dye molecules having two or more heterocyclic rings each incorporating sulfur atoms (hereinafter "multi-heterosulfur organic dyes"), benzotriazole dyes, combinations thereof, and the like. In certain embodiments, the Raman reporter molecule includes resonant Raman reporters, which have strong electronic transitions in the visible spectrum, such that resonance Raman enhancement can be used to further amplify the signal intensities.

The resonant Raman reporters may include, but are not limited to, organic dyes, biomolecules, porphyrins, metalloporphyrins, combinations thereof, and the like. In some instances, the resonant Raman reporters include, but are not limited to, malachite green isothiocyanate (MGITC), tetramethylrhodamine-5-isothiocyante (TRITC), X-rhodamine-5-isothiocyanate and X-rhodamine-6-isothiocyanate (XRITC), 3,3'-diethylthiadicarbocyanine iodide (DTDC), and combinations thereof.

In certain embodiments, the Raman reporter molecule includes, but is not limited to, thiacyanine dyes, dithiacyanine dyes, thiacarbocyanine dyes (e.g., thiacarbocyanine dyes, thiadicarbocyanine dyes, and thiatricarbocyanine dyes), and dithiacarbocyanine dyes (e.g., dithiacarbocyanine dyes, dithiadicarbocyanine dyes, and dithiatricarbocyanine dyes), combinations thereof, and the like.

Furthermore, the Raman reporter molecule can include, but is not limited to, one or more of the following: 3,3'-diethyl-9-methylthiacarbocyanine iodide; 1,1'-diethyl-2,2'-quinotricarbocyanine iodide; 3,3'-diethylthiacyanine iodide; 4-acetamido-4'-isothiocyanatostilbene-2,2'-disulfonic acid, disodium salt; benzophenone-4-isothiocyanate; 4,4'-diisothiocyanatodihydrostilbene-2,2'-disulfonic acid, disodium salt; 4,4'-diisothiocyanatostilbene-2,2'-disulfonic acid, disodium salt; N-(4-(6-dimethylamino-2-benzofuranyl)phenylisothiocyanate; 7-dimethylamino-4-methylcoumarin-3-isothiocyanate; eosin-5-isothiocyanate; erythrosin-5-isothiocyanate; fluorescein-5-isothiocyanate; (S)-1-p-isothiocyanatobenzyldiethylenetriaminepentaacetic acid; Oregon Greens 488 isothiocyanate; tetramethylrhodamine-5-isothiocyanate; tetramethylrhodamine-6-isothiocyanate; tetramethylrhodamine-5- (and -6)-isothiocyanate; X-rhodamine-5- (and -6)-isothiocyanate, combinations thereof, and the like.

The benzotriazole dyes can include, but are not limited to, azobenzotriazoyl-3,5-dimethoxyphenylamine, dimethoxy-4-(6'-azobenzotriazolyl)phenol, combinations therefore, and the like.

In certain embodiments, the coating includes an encapsulating material. The encapsulating material may include materials such as, but not limited to, silica, polymers (e.g., synthetic polymers, biopolymers, etc.), metal oxides (e.g., iron oxide, copper oxide, titanium dioxide, metal sulfides, combinations thereof, etc.), metal sulfides, peptides, proteins, carbohydrates, lipids, nucleic acids, salt complexes of each of these, combinations thereof, and the like.

In some instances, the SERS labels are spherical and have an average diameter of 250 nm or less, such as 150 nm or less, 100 nm or less, 50 nm or less. In certain cases, the SERS labels have an average diameter of 5 nm to 250 nm, such as 10 nm to 150 nm, including 30 nm to 90 nm. For example, the SERS labels may have an average diameter of 50 nm.

In certain embodiments, the optical label includes a charged label. Charged labels are labeling moieties that have a net positive or negative charge. Charged labels may include any of the optical labels described above that have a net positive or negative charge. For instance, in certain embodiments, the charged label has a net positive charge. In other cases, the charged label has a net negative charge. Charged labels may be detectable when sufficiently associated with a proximity sensor (e.g., a surface plasmon resonance (SPR) detector). For example, the presence of a charged label near the surface of a SPR detector may induce a detectable change in the surface plasmon resonance of the detector. Charged labels of interest may be sufficiently associated with a proximity sensor if the distance between the center of the charged label and the surface of the sensor is 200 nm or less, such as 150 nm or less, including 100 nm or less.

Fluorescent Labels

In certain embodiments, the proximity label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.).

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2' disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7' dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof; and the like.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

Sensors

As described above, embodiments of the subject methods include providing a sensor, such as a proximity sensor, in contact with an assay composition that includes a sample and a proximity label. Depending on a given embodiment, a variety of different types of sensors may be employed. For example, sensors may be proximity or non-proximity type sensors. For example, non-proximity type sensors may employ an imaging device (e.g., CCD camera) with fluorescent or Raman labels. In certain instances, the sensor is a proximity sensor. For ease of description, aspects of the invention are now further described in the context of proximity sensors.

In some cases, proximity sensors are sensors configured to detect the presence of nearby proximity labels without any direct physical contact between the proximity sensor and the proximity label. In certain embodiments, the proximity sensors are configured to detect the presence of an analyte in a sample. For example, a proximity label may be bound, either directly or indirectly, to an analyte, which in turn may be bound, either directly or indirectly, to the proximity sensor. If the bound proximity label is positioned within the detection range of the proximity sensor, then the proximity sensor may provide a signal indicating the presence of the bound proximity label, and thus indicating the presence of the analyte.

In some instances, the proximity sensors have a detection range from 1 nm to 200 nm from the surface of the proximity sensor, such as from 5 nm to 150 nm, including from 5 nm to 100 nm, such as from 5 nm to 50 nm, including from 5 nm to 25 nm from the surface of the proximity sensor. By "detection range" is meant the distance from the surface of the proximity detector where the presence of a proximity label will induce a detectable signal in the proximity detector. In some cases, proximity labels positioned close enough to the surface of the proximity sensor to be within the detection range of the proximity sensor will induce a detectable signal in the proximity sensor. In certain instances, proximity labels positioned at a distance from the surface of the proximity sensor that is greater than the detection range of the proximity sensor will not induce a detectable signal in the proximity sensor. For example, a magnetic label may have a magnetic flux that is proportional to $1/r^3$, where r is the distance between the proximity sensor and the magnetic label. Thus, only those magnetic labels that are positioned in close proximity (e.g., within the detection range of the proximity sensor) will induce a detectable signal in the proximity sensor.

In certain embodiments, the surface of the proximity sensor is functionalized to bind directly to an analyte. For example, the surface of the proximity sensor may be functionalized to provide for covalent binding or non-covalent association of the analyte and proximity sensor, including, but not limited to, non-specific adsorption, binding based on electrostatic (e.g., ion-ion pair interactions), hydrophobic interactions, hydrogen bonding interactions, and the like.

In some instances, the surface of the proximity sensor includes a surface capture ligand that specifically binds to an analyte. The surface capture ligand may be bound to the surface of the proximity sensor. For instance, a cationic polymer such as polyethyleneimine (PEI) can be used to nonspecifically bind charged antibodies to the sensor surface via physabsorption. Alternatively, a covalent chemistry can be used utilizing free amines or free thiol groups on the surface capture ligand to covalently bind the surface capture ligand to the surface of the proximity sensor. For example, an N-hydroxysuccinimide (NHS) to 1-ethyl-3-(3-dimethylaminopropyl)carbodiimide (EDC) coupling system may be used to covalently bind the surface capture ligand to the surface of the proximity sensor.

The surface capture ligand may include one member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like. In certain embodiments, the surface of the proximity sensor includes an antibody that specifically binds to an analyte of interest. Accordingly, contacting the proximity sensor with an assay composition that includes the analyte of interest may result in binding of the analyte to the surface capture ligand (e.g., antibody) bound to the surface of the proximity sensor.

Proximity sensors that may be used in the subject methods may vary, and include any type of sensor that provides a detectable signal when a proximity label is positioned near the surface of the proximity sensor. For example, proximity sensors may include, but are not limited to: magnetic sensors (e.g., giant magnetoresistive (GMR) sensors, such as spin valve detectors, magnetic tunnel junction (MTJ) detectors, etc.); surface plasmon resonance (SPR) detectors; fluorescence detectors; and the like. Each of these types of proximity sensors are discussed in more detail below.

Magnetic Sensors

In certain embodiments, the proximity sensor is a magnetic sensor. Magnetic sensors may be configured to generate an electrical signal in response to a magnetic label in proximity to a surface of the magnetic sensor. Magnetic sensors may include, but are not limited to, magnetoresistive sensor devices, including giant magnetoresistive (GMR) sensors. For example, the magnetic sensors may be configured to detect changes in the resistance of the magnetic sensor induced by changes in the local magnetic field. In some cases, binding of a proximity label (e.g., a magnetic label) in close proximity to the magnetic sensor, as described above, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. In certain embodiments, the magnetic sensors are configured to detect changes in resistance of 1 Ohm or less, such as 500 mOhm or less, including 100 mOhm or less, or 50 mOhm or less, or 25 mOhm or less, or 10 mOhm or less, or 5 mOhm or less, or 1 mOhm or less.

In certain cases, GMR sensors are multilayer thin film structures. GMR sensors may include alternating layers of a ferromagnetic material and a non-magnetic material. The ferromagnetic material may include, but is not limited to, Permalloy (NiFe), iron cobalt (FeCo), nickel iron cobalt (NiFeCo), nickel oxide (NiO), cobalt oxide (CoO), nickel cobalt oxide (NiCoO), ferric oxide ($Fe_2O_3$), and the like.

In some cases, the non-magnetic material is a conductive nonmagnetic material, such as, but not limited to copper, gold, silver, etc.

In certain embodiments, the ferromagnetic layer has a thickness of 1 nm to 50 nm, such as 5 nm to 25 nm, including 5 nm to 10 nm. In some instances, the nonmagnetic layer has a thickness of 1 nm to 50 nm, such as 1 nm to 25 nm, including 1 nm to 10 nm.

In some cases, GMR sensors include, but are not limited to spin valve detectors and magnetic tunnel junction (MTJ) detectors, each of which are discussed in more detail below.

Spin-Valve Detectors

In some instances, the magnetic sensor is a spin valve detector. In certain case, the spin valve detector is a multilayer structure that includes a first ferromagnetic layer, a non-magnetic layer disposed on the first ferromagnetic layer, and a second ferromagnetic layer disposed on the non-magnetic layer. The first ferromagnetic layer may be configured to have its magnetization vector fixed in a certain direction. In some cases, the first ferromagnetic layer is called the "pinned layer". The second ferromagnetic layer may be configured such that its magnetization vector can rotate freely under an applied magnetic field. In some cases, the second ferromagnetic layer is called the "free layer".

In certain instances, the electrical resistance of a spin valve detector depends on the relative orientation of the magnetization vector of the free layer to that of the pinned layer. When the two magnetization vectors are parallel, the resistance is the lowest; when the two magnetization vectors are antiparallel, the resistance is the highest. The relative change of resistance is called the magnetoresistance (MR) ratio. In certain embodiments, spin valve detectors have a MR ratio of 1% to 20%, such as 3% to 15%, including 5% to 12%. In some cases, the MR ratio of a spin valve detector is 10% or more in a small magnetic field, e.g., 100 Oe. Changes in the resistance of the spin valve detector due to the presence of magnetic labels near the surface of the spin valve detector may be detected, as described above.

In certain embodiments, the signal from the spin valve detector due to the magnetic label depends on the distance between the magnetic label and the free layer of the spin valve detector. In some cases, the voltage signal from a magnetic label decreases as the distance from the center of the magnetic label to the mid-plane of the free layer increases. Thus, in certain instances, the free layer in the spin valve detector is positioned at the surface of the spin valve detector. Positioning the free layer at the surface of the spin valve detector may minimize the distance between the free layer and any bound magnetic labels, which may facilitate detection of the magnetic labels.

In certain embodiments, the spin valve detector may include a passivation layer disposed on one or more of the spin valve detector surfaces. In some cases, the passivation layer has a thickness of 60 nm or less, such as 50 nm or less, including 40 nm or less, 30 nm or less, 20 nm or less, 10 nm or less. For instance, the passivation layer may have a thickness of 1 nm to 10 nm, such as from 1 nm to 5 nm, including from 1 nm to 3 nm. In certain embodiments, the passivation layer includes gold, tantalum, $SiO_2$, $Si_3N_4$, combinations thereof, and the like.

Magnetic Tunnel Junction Detectors

In certain embodiments, the magnetic sensor is a magnetic tunnel junction (MTJ) detectors. In some cases, the MTJ detectors include a multilayer structure that includes a first ferromagnetic layer, an insulating layer disposed on the first ferromagnetic layer, and a second ferromagnetic layer disposed on the insulating layer. The insulating layer may be a thin insulating tunnel barrier, and may include alumina, MgO, and the like. In some cases, electron tunneling between the first and the second ferromagnetic layers depends on the relative magnetization of the two ferromagnetic layers. For example, in certain embodiments, the tunneling current is high when the magnetization vectors of the first and second ferromagnetic layers are parallel and the tunneling current is low when the magnetization vectors of the first and second ferromagnetic layers antiparallel.

In some instances, MTJ detectors have a MR ratio of 1% to 300%, such as 10% to 250%, including 25% to 200%. Changes in the resistance of the MTJ detector due to the presence of magnetic labels near the surface of the MTJ detector may be detected, as described above.

In certain embodiments, the second ferromagnetic layer (e.g., the layer of the MTJ detector positioned at the surface of the MTJ detector) includes two of more layers. For example, the second ferromagnetic layer may include a first layer and a second layer disposed on the first layer. In some cases, the first layer is a thin metallic layer (e.g., a gold layer). The thin metallic layer may have a thickness of 60 nm or less, such as 50 nm or less, including 40 nm or less, 30 nm or less, 20 nm or less, or 10 nm or less. The second layer may include a conductive metal, e.g., copper, aluminum, palladium, palladium alloys, palladium oxides, platinum, platinum alloys, platinum oxides, ruthenium, ruthenium alloys, ruthenium oxides, silver, silver alloys, silver oxides, tin, tin alloys, tin oxides, titanium, titanium alloys, titanium oxides, combinations thereof, and the like.

In some cases, the MTJ detector is configured such that the distance between an associated magnetic label and the top surface of the free layer ranges from 1 nm to 200 nm, such as from 5 nm to 150 nm, including from 5 nm to 100 nm, such as from 5 nm to 50 nm, including from 5 nm to 25 nm.

As described above for spin valve detectors, in certain instances, MTJ detectors may include a passivation layer disposed on one or more of the MTJ detector surfaces. In some instances, the passivation layer has a thickness of 60 nm or less, such as 50 nm or less, including 40 nm or less, 30 nm or less, 20 nm or less, 10 nm or less. For example, the passivation layer may have a thickness of 1 nm to 10 nm, such as from 1 nm to 5 nm, including from 1 nm to 3 nm. In some cases, the passivation layer includes gold, tantalum, $SiO_2$, $Si_3N_4$, combinations thereof, and the like.

Spin valve detectors (also referred to as spin valve film detectors) and magnetic tunnel junction (MTJ) detectors, are further described in U.S. Ser. No. 12/234,506, filed Sep. 19, 2008, and entitled "Analyte Detection with Magnetic Sensors", the disclosure of which is hereby incorporated by reference in its entirety. Detectors are further described in U.S. patent application Ser. No. 10/829,505, filed Apr. 22, 2004 and entitled "Magnetic nanoparticles, magnetic detector arrays, and methods for their use in detecting biological molecules", the disclosure of which is hereby incorporated by reference in its entirety.

Surface Plasmon Resonance (SPR) Detectors

In certain embodiments, the proximity sensor includes a surface plasmon resonance (SPR) detector. Surface plasmon resonance refers to a quantum mechanical effect where surface plasmons, e.g., surface electromagnetic waves, are excited in a resonant manner by electrons or light (e.g., visible or IR). In some cases, the surface plasmons propagate along the surface of the proximity sensor. If the surface plasmons contact an irregularity on the surface of the proximity sensor, the surface plasmons may emit part of their energy as light. In certain instances, the irregularities on the surface of the proximity sensor include molecules bound to the surface of the proximity sensor, such as, an analyte of interest directly or indirectly bound to the surface of the proximity sensor, as described above. Surface plasmon emissions may be detected by an appropriate detector to determine the presence of an analyte in close proximity to the surface of the proximity sensor. In certain embodiments, the surface-bound analyte of interest may be bound to a proximity label, such as a SERS label, as described above. In some cases, the presence of a SERS label near the surface of a SPR detector may induce a detectable enhancement of Raman scattering by the SERS label.

Surface plasmon resonance detectors may include a metal film disposed on the surface of a substrate. In certain cases, the metal film includes metals, such as, but not limited to, silver, gold, copper, titanium, chromium, and the like. Certain embodiments of the metal films have thicknesses ranging from 1 nm to 100 nm, such as 5 nm to 75 nm, including from 10 nm to 50 nm.

In some instances, the surface plasmon resonance detectors include a detector. The detector may be configured to detect surface plasmon emissions, as described above. In certain cases, the detector includes a photomultiplier tube (PMT), a charge-coupled device (CCD), an intensified charge-coupled device (ICCD), a complementary metal-oxide-semiconductor (CMOS) sensor, and the like.

Fluorescence Detectors

In some cases, the proximity sensor includes a fluorescence detector. As discussed above, certain embodiments of the proximity labels include fluorescent labels, which may be bound directly or indirectly to an analyte of interest, which in turn may be bound directly or indirectly to the surface of the proximity sensor. In some instances, the fluorescently labeled analyte that is bound to the surface of the proximity sensor is detected by a fluorescence detector. For example, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector to determine the presence of the analyte on the surface of the proximity sensor.

In some instances, the fluorescence detectors include a detector. The detector may be configured to detect emissions from the fluorescent labels, as described above. In certain cases, the detector includes a photomultiplier tube (PMT), a charge-coupled device (CCD), an intensified charge-coupled device (ICCD), a complementary metal-oxide-semiconductor (CMOS) sensor, and the like.

Assay Composition Production

As described above, embodiments of the subject methods include providing a proximity sensor in contact with an assay composition. In certain cases, the assay composition includes a sample and a proximity label. Embodiments of the sample and the proximity label are discussed in detail above.

In some instances, the method includes producing the assay composition by sequentially contacting the proximity sensor with the sample and the proximity label. As such, the method may include producing the assay composition in situ on the surface of the proximity sensor. For example, the method may include contacting the proximity sensor first with the sample and subsequently with the proximity label. Alternatively, the method may include contacting the proximity sensor first with the proximity label and subsequently with the sample.

In other embodiments, the method includes combining the sample and the proximity label to produce the assay composition and then contacting the assay composition with the proximity sensor. For instance, the method may include first combining the sample and the proximity label in a separate container to produce the assay composition. Then the assay composition may be contacted with the proximity sensor, as described above. Subsequently, the method may include introducing a capture probe into the assay composition, as described in detail below.

Introduction of a Capture Probe into the Assay Composition

Aspects of the subject methods include introducing a capture probe into the assay composition. As described above, the assay composition may include a sample and a proximity label. In certain embodiments, the capture probe is configured to bind to the proximity label and an analyte in the sample.

Capture Probe

A capture probe can be any molecule that specifically binds to a protein or nucleic acid sequence that is being targeted (e.g., the analyte of interest). Depending on the nature of the analyte, capture probes can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the capture probe includes an antibody. The capture probe antibody may specifically bind to an analyte of interest. In some cases, the capture probe is a modified antibody. The modified antibody may be configured to specifically bind to the analyte of interest and may also include one or more additional members of a specific binding pair. The one or more members of a specific binding pair may be configured to specifically bind to a complementary member of the specific binding pair. In certain instances, the complementary member of the specific binding pair is bound to the proximity label, as described above. For example, the capture probe may be an antibody that specifically binds to an analyte of interest. In addition, the capture probe may be modified to include biotin. As described above, in certain embodiments, proximity labels may be modified to include streptavidin. As such, the capture probe may be configured to specifically bind to the analyte of interest (e.g., through an antibody-antigen interaction) and to specifically bind to the proximity label (e.g., through a streptavidin-biotin interaction). In some cases, the capture probe is configured to bind to the analyte of interest and the proximity label. Stated another way, the capture probe may be configured such that specific binding of the analyte to the capture probe does not significantly interfere with the ability of the capture probe to specifically bind to the proximity label. Similarly, the capture probe may be configured such that specific binding of the proximity label to the capture probe does not significantly interfere with the ability of the capture probe to specifically bind to the analyte.

Introduction of a capture probe into the assay composition allows the capture probe to specifically bind to an analyte of interest. In some cases, the capture probe can be identified so that the presence of the analyte of interest can then be detected. Capture probes may be identified by any of the methods described herein. For example, as described above, analytes may be directly or indirectly bound to a proximity sensor of choice (e.g., magnetic sensor, fluorescence detector, surface plasmon resonance detector). After introduction of a capture probe into the assay composition, the capture probe may contact and specifically bind to the analyte of interest. As indicated above, the capture probe may be configured to bind to a proximity label and the analyte of interest. In certain instances, simultaneous binding of the capture probe to surface-bound analyte and the proximity label positions the proximity label within the detection range of the proximity sensor, such that a detectable signal is induced in the proximity sensor.

In some cases, false-positive signals due to non-specific binding of the capture probe to moieties not of interest are minimized. For example, non-specific binding of the capture probe to other moieties not of interest, which are not bound to the surface of the proximity sensor and remain in solution, will not induce a detectable signal in the proximity sensor because the proximity label bound to the capture probe will not be positioned within the detection range of the proximity sensor.

As described above, the proximity label may be colloidal, such that the proximity label remains dispersed in the assay composition solution. In certain instances, the kinetics of the capture probe diffusion to the surface of the proximity sensor and binding to the analyte is significantly faster than the kinetics of the diffusion of the proximity labels to the surface of the proximity sensor. Having faster kinetics for the binding of the capture probe to the analyte than the diffusion of the proximity label to the surface of the proximity sensor may facilitate a minimization in false positive signals due to non-specific positioning of the proximity label within the detection range of the proximity sensor.

Process for Introducing the Capture Probe into the Assay Composition

As discussed above, the methods include introducing the capture probe into the assay composition. In certain embodiments, the capture probe is added to the assay composition after the assay composition is contacted to the proximity sensor. Thus, the methods may include first producing an assay composition that includes a sample and a proximity label. The assay composition may then be contacted with the proximity sensor. Subsequently, a capture probe may be introduced into the assay composition.

Other methods are also possible. For example, the method may include first producing the assay composition, where the assay composition includes a sample and a proximity label. Then, introducing the capture probe to the assay composition, and subsequently contacting the assay composition to the proximity sensor. In both of the methods described above, the proximity label is present in the assay composition prior to the addition of the capture probe to the assay composition.

The capture probe may be introduced into the assay composition by any convenient fluid handling method. For example, introducing the capture probe into the assay composition may include, but is not limited to, the use of syringes, pipettes, eyedroppers, ampoules, or other fluid handling components, such as microfluidic fluid handling components.

As described above, in some instances, the methods are wash-free methods of determining the presence of one or more analytes in a sample. As such, in certain embodiments, introducing the capture probe into the assay composition does not include any washing steps before or after the capture probe is introduced into the assay composition. Thus, no washing step is performed either before or after the proximity sensor is contacted with the capture probe.

Obtaining a Signal to Determine the Presence of One or More Analytes in a Sample Embodiments of the subject methods also include obtaining a signal from a proximity sensor to detect the presence of an analyte in a sample. As described above, a proximity label may be bound, either directly or indirectly, to the analyte, which in turn may be bound, either directly or indirectly, to the proximity sensor. If the bound proximity label is positioned within the detection range of the proximity sensor, then the proximity sensor may provide a signal indicating the presence of the bound proximity label, and thus indicating the presence of the analyte.

As indicated above, various types of proximity sensors may be used in the subject methods and systems, such as, but not limited to magnetic sensors, surface plasmon resonance detectors, fluorescence detectors, and the like. Magnetic sensors may be configured to generate an electrical signal in response to a magnetic label in proximity to a surface of the magnetic sensor. For example, a change in the resistance of the magnetic sensor may be induced by changes in the local magnetic field. In some cases, binding of a proximity label (e.g., a magnetic label) in close proximity to the magnetic sensor induces a detectable change in the local magnetic field of the magnetic sensor. For example, the magnetic field created by the magnetic labels that are bound to the analytes of interest may exceed the magnetic field that is created by unbound magnetic labels that remain dispersed in the sample. Changes in the local magnetic filed of the magnetic sensor may be detected as a change in the resistance of the magnetic sensor.

In certain embodiments, the proximity label is an optical label, such as a surface enhanced Raman spectroscopy (SERS) label, and the proximity sensor is a surface plasmon resonance (SPR) detector. As described above, if the surface plasmons in the SPR detector contact an irregularity on the surface of the sensor, the surface plasmons may emit part of their energy as light. Irregularities on the surface of the proximity sensor may include molecules bound to the surface of the proximity sensor, such as, an analyte of interest directly or indirectly bound to the surface of the proximity sensor, and proximity labels directly or indirectly bound to the analyte of interest that are positioned within the detection range of the proximity sensor. Surface plasmon emissions may be detected by an appropriate detector, such as a photomultiplier tube (PMT), a charge-coupled device (CCD), an intensified charge-coupled device (ICCD), a complementary metal-oxide-semiconductor (CMOS) sensor, and the like, to determine the presence of an analyte in close proximity to the surface of the proximity sensor.

In certain embodiments, the proximity label is a fluorescent label and the proximity sensor is a fluorescence detector. As described above, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector, such as a PMT, a CCD, an ICCD, a CMOS sensor, and the like, to determine the presence of the analyte on the surface of the proximity sensor.

Aspects of the methods may also include obtaining a real-time signal from the device. As such, embodiments of the method include obtaining a real-time signal from the proximity sensor. By "real-time" is meant that a signal is observed as it is being produced or immediately thereafter. Accordingly, certain embodiments include observing the evolution in real time of the signal associated with the occurrence of the binding interaction of interest (e.g., the binding of the analyte of interest to the proximity sensor). The real-time signal may include two or more data points obtained over a given period of time, where in certain embodiments the signal obtained is a continuous set of data points (e.g., in the form of a trace) obtained continuously over a given period of time of interest. The time period of interest may vary, ranging in some instances from 0.5 min to 60 min, such as 1 min to 30 min, including 5 min to 15 min. The number of data points in the signal may also vary, where in some instances, the number of data points is sufficient to provide a continuous stretch of data over the time course of the real-time signal.

In some embodiments, the signal is observed while the assay device is in a wet condition. By "wet" or "wet condition" is meant that the assay composition (e.g., an assay composition that includes a sample, a proximity label, and a capture probe) is still in contact with the surface of the proximity sensor. As such, there is no need to perform any washing steps to remove the non-binding moieties that are not of interest or the excess proximity labels or capture probes. In certain embodiments, the use of proximity labels and proximity sensors, as described above, facilitates "wet" detection because the signal induced in the proximity sensor by the proximity label decreases as the distance between the proximity label and the surface of the proximity sensor increases. For example, the use of magnetic proximity labels and magnetic sensors, as described above, may facilitate "wet" detection because the magnetic field generated by the magnetic labels decreases as the distance between the magnetic label and the surface of the magnetic sensor increases. In some instances, the magnetic field of the magnetic label bound to the surface-bound analyte exceeds the magnetic field from the unbound magnetic labels dispersed in solution. The unbound magnetic labels dispersed in solution may be at a greater distance from the surface of the magnetic sensor and may be in Brownian motion, which may reduce the ability of the unbound magnetic labels to induce a detectable change in the resistance of the magnetic sensor.

For a given binding interaction of interest, the methods may include obtaining a real-time signal for a single binding pair member concentration or multiple binding pair concentrations, such as 2 or more, 3 or more, 5 or more, 10 or more different binding pair concentrations. For example, a given assay may contact the same sensor having the same capture probe concentration with multiple different binding pair member concentrations, or vice versa, or a combination of different concentrations of capture probes and binding pair members, as desired.

FIG. 1 shows an illustration of a method of detecting the presence of an analyte in a sample according to embodiments of the present disclosure. In the first step of the method (FIG. 1(a)), a proximity sensor 10 is provided in contact with as assay composition 16 that includes an analyte of interest 12. The surface of the proximity sensor 10 is modified to include surface capture ligands 11 that specifically bind to the analyte 12. The assay composition 16 may also include other moieties 13 that do not specifically bind to the surface capture ligands 11. As shown in FIG. 1(b), the analyte 12 specifically binds to the surface capture ligand 11, thus binding the analyte to the surface of the proximity sensor 10. The other moieties 13 that are non-complementary to the surface capture ligand 11 will not bind to the surface capture ligand 11 and will remain in solution. In the second step of the method (FIG. 1(c)), proximity labels 14 are added to the assay composition 16. In the embodiment shown in FIG. 1, the proximity labels 14 are magnetic labels modified with streptavidin (not shown). The proximity labels 14 are colloidal and, as such, the proximity labels 14 remain dispersed in the assay composition 16 and do not settle on the surface of the proximity sensor 10. Thus, as shown in FIG. 1(c) the proximity labels 14 are dispersed in the assay composition 16 and are not positioned within the detection range of the proximity sensor 10 in a significantly detectable amount. In the third step of the method (FIG. 1(d)), capture probes 15 are introduced into the assay composition 16. The capture probes 15 specifically bind to the analyte 12. In addition, the capture probes 15 are modified to include biotin. As shown in FIG. 1(e), the streptavidin-labeled proximity labels 14 specifically bind to the biotinylated capture probes 15. Thus, the proximity labels 14 will be specifically bound to the capture probes 15 via the streptavidin-biotin interaction. After binding of the proximity label 14 to the capture probe 15, the proximity label 14 is held in close enough proximity to the surface of the proximity sensor 10 to be within the detection range of the proximity sensor 10. In the embodiment shown in FIG. 1, the proximity sensor 10 is a magnetic sensor (e.g., a giant magnetoresistive (GMR) sensor). When the proximity label 14 is within the detection range of the proximity sensor 10, the proximity label 14 can induce a detectable signal in the proximity sensor 10.

Where desired, the above analyte detection method may be carried out with the aid of software and/or hardware configured to perform the above described protocol. For example, in certain embodiments, the method of detecting the presence of an analyte in a sample includes the following: providing a hand-held analyte detection device that includes a sample receiving member and a proximity sensor associated with the sample receiving member such that when the sample is placed in the sample receiving member the sample contacts the proximity sensor; producing an assay composition in contact with the proximity sensor, where the assay composition includes the sample and a proximity label; introducing a capture probe into the assay composition, where the capture probe is configured to bind to the proximity label and the analyte; operably coupling the analyte detection device to an activation and signal processing unit; and receiving an analyte detection result from the activation and signal processing unit. Additional aspects of the devices and systems are discussed in more detail below.

Antibody Cross-Reactivity

Aspects of the methods include detecting antibody cross-reactivity. Antibody cross-reactivity refers to the binding between an antigen and an antibody that is specific for a different but similar antigen. For example, an antibody may specifically bind to an antigen at a particular epitope. In addition, the antibody may also specifically bind to a similar epitope on a different antigen. The binding of the antibody to the similar epitope on a different antigen is called antibody cross-reactivity. In certain embodiments, the device for detecting the presence of an analyte in a sample includes an array of proximity sensors. In some cases, each proximity sensor has a different surface capture ligand associated with its surface, such that each different surface capture ligand specifically binds to a distinct analyte. In certain instances, the method includes contacting the array of proximity sensors with an assay composition that includes a sample and a proximity label. The sample may include two or more different analytes, which specifically bind to the corresponding antibodies in the array. In some cases, the method further includes sequentially introducing capture probes into the assay composition, where each different capture probe is configured to specifically bind to a distinct analyte. Each capture probe is also configured to bind to the proximity label to produce a detectable signal, as described above. The method may also include obtaining a signal from the proximity sensor, as described above. By sequentially introducing each capture probe into the assay composition, the specific binding of each capture probe to its corresponding analyte can be detected as a signal at a particular proximity sensor in the array. In addition, any cross-reactivity between the capture probe and other analytes can also be detected as signals at other proximity sensors in the array. In certain embodiments, no washing steps are performed between the introduction of each capture probe. For example, each capture probe may be sequentially added to the assay composition without any washing steps.

In certain embodiments, the method includes contacting the array of proximity sensors with an assay composition that includes a proximity label. The method may also include introducing two or more different capture probes into the assay composition, where each different capture probe is configured to specifically bind to a distinct analyte. In some cases, the method includes sequentially introducing two or more analytes into the assay composition. Upon introduction of the analyte to the assay composition, the analyte may specifically bind to its corresponding surface capture ligand and its corresponding capture probe. Similar to the method described above, by sequentially introducing each analyte into the assay composition, the specific binding of each analyte to its corresponding capture probe can be detected as a signal at a particular proximity sensor in the array. In addition, any cross-reactivity between the capture probe and other analytes can also be detected as signals at other proximity sensors in the array. In certain embodiments, no washing steps are performed between the introduction of each analyte. For example, each analyte may be sequentially added to the assay composition without any washing steps.

Devices and Systems

Aspects of the present disclosure further include devices and systems for detecting the presence of an analyte in a sample. Representative embodiments of the subject devices and systems are presented in more detail below.

Devices

Devices for detecting the presence of an analyte in a sample include a sample receiving member and a proximity sensor, as described above. The proximity sensor is associated with the sample receiving member such that, when the sample is placed in the sample receiving member, the sample contacts the proximity sensor. Additional aspects of the subject proximity sensor devices are described below.

The sample receiving member may be any of a variety of configurations, where the sample receiving member is configured to hold the sample in contact with the proximity sensor. Accordingly, configurations of the sample receiving member may include, but are not limited to: well configurations in which the proximity sensor is associated with the bottom or sides of a well; sample receiving members that include one or more walls that extend above the surface of the proximity sensor; and the like. For instance, the sample receiving member may include walls that surround the proximity sensor and that extend above the surface of the proximity sensor. The walls may be substantially vertical with respect to the surface of the proximity sensor. In some cases, the walls of the sample receiving member define a volume of space above the surface of the proximity sensor that may receive a volume of sample equal to or less than the volume of space defined by the sample receiving member.

In certain embodiments, the device is configured to produce a detectable signal from a minimum amount of sample. In some instances, the device is configured to produce a detectable signal from a sample size of 1 mL or less, such as 500 µL or less, including 100 µL or less, for example 50 µL or less, or 25 µL or less, or 10 µL or less. As such, in some cases, the sample receiving member is configured to receive a minimum amount of sample needed to produce a detectable signal. For example, the sample receiving member may be configured to receive a sample of 1 mL or less, such as 500 µL or less, including 100 µL or less, for example 50 µL or less, or 25 µL or less, or 10 µL or less.

As described above, the device for detecting the presence of an analyte in a sample may include a sample receiving member and a proximity sensor. In some cases, the proximity sensor is a magnetic sensor, as described above. In some embodiments, the device is configured to connect to a system for detecting the presence of an analyte in a sample. Accordingly, in certain embodiments, the device does not include a magnetic field generator. The magnetic field generator may be included in the system for detecting the presence of an analyte in the sample and not included in the device. Thus, the assay protocol may include operably coupling the analyte detection device to the system for detecting the presence of an analyte in the sample. In some instances, the analyte detection device may be operably coupled to an activation and signal processing unit of the system, as described further below.

In certain embodiments, the device for detecting the presence of an analyte in a sample is configured to be a portable device. By "portable" is meant that the device can be hand-held, used on a lap, or wearable, such as worn in a pocket, belt, or the like. As such, the devices of these embodiments are dimensioned and configured to be portable. In some instances, the devices have a length ranging from 1 mm to 700 mm, such as 10 mm to 300 mm and including 25 mm to 125 mm; a width ranging from 1 mm to 700 mm, such as 10 mm to 300 mm and including 25 mm to 125 mm; and a height ranging from 1 mm to 700 mm, such as 10 mm to 300 mm and including 25 mm to 125 mm. As the device may be portable, the have a weight suitable to be carried by an average human without exerting substantially noticeable effort, and in some instances the devices weigh 10 lbs or less, such as 5 lbs or less, including 2 lbs or less, 1 lb or less and even 0.5 lb or less. Portable devices may be operated in clinical or laboratory settings, where the portable size of the device may facilitate ease of use and transportability of the device between clinical or laboratory settings. In certain cases, portable devices may be operated without requiring a clinical or laboratory setting for implementation. For example, portable devices may be used in field settings or remote locations where technicians and laboratory equipment may be unavailable. In some instances, the device is configured to be a hand-held device. Accordingly, the sample receiving member and the proximity sensor of the device may be present in a hand-held housing.

Proximity Sensor Device Configurations

The proximity sensor devices may have a variety of different configurations, e.g., with respect to sensor configuration. In some cases, the proximity sensor devices may have different configurations depending on whether the devices are configured for batch or flow through use, etc. As such, any configuration that provides a proximity sensor of the device to come into contact with an assay composition that includes a sample and a proximity label may be employed. Accordingly, configurations may include, but are not limited to: well configurations (in which the sensor is associated with the bottom or walls of a sample receiving member, such as a well); flow through configurations, e.g., where the sensor is associated with a wall of a flow cell having a fluid input and output; and the like.

In certain embodiments, the subject proximity sensor device is a biochip (e.g., a biosensor chip). By "biochip" or "biosensor chip" is meant a proximity sensor device that includes a substrate surface which displays two or more distinct proximity sensors on the substrate surface. In certain embodiments, the proximity sensor device includes a substrate surface with an array of proximity sensors.

An "array" includes any two-dimensional or substantially two-dimensional (as well as a three-dimensional) arrangement of addressable regions, e.g., spatially addressable regions. An array is "addressable" when it has multiple sensors positioned at particular predetermined locations (e.g., "addresses") on the array. Array features (e.g., sensors) may be separated by intervening spaces. Any given substrate may carry one, two, four or more arrays disposed on a front surface of the substrate. Depending upon the use, any or all of the arrays may be the same or different from one another and each may contain multiple distinct proximity sensors. An array may contain one or more, including two or more, four or more, 8 or more, 10 or more, 50 or more, or 100 or more proximity sensors. For example, 64 proximity sensors can be arranged into an 8×8 array. In certain embodiments, the proximity sensors can be arranged into an array with an area of less than 10 $cm^2$, or less than 5 $cm^2$, e.g., less than 1 $cm^2$, including less than 50 $mm^2$, less than 20 $mm^2$, such as less than 10 $mm^2$, or even smaller. For example, proximity sensors may have dimensions in the range of 10 µm×10 µm to 200 µm×200 µm, including dimensions of 100 µm×100 µm or less, such as 75 µm×75 µm or less, for instance 50 µm×50 µm or less.

As discussed above, at least some, or all, of the proximity sensors have a surface capture ligand stably associated with a surface of the sensor. Where a given device includes two or more proximity sensors, each sensor may have the same or different surface capture ligand associated with its surface. Accordingly, different surface capture ligands may be present on the sensor surfaces of such devices, such that each different surface capture ligand specifically binds to a distinct analyte. In other cases, the proximity sensor devices include proximity sensors that are free of any surface capture ligands, such that the surface of the proximity sensor is functionalized to bind directly to the analyte. In some instances, the proximity sensor includes a blocking layer disposed over the surface of the proximity sensor. The blocking layer may be configured to inhibit the binding of any surface capture ligands or analyte to the surface of the proximity sensor (e.g., where such blocked proximity sensors may serve as sources of reference or control electrical signals).

In multi-sensor devices, areas in between the proximity sensors may be present which do not carry any surface capture ligands or are not functionalized to bind directly to the analyte. Such inter-sensor areas, when present, may be of various sizes and configurations. In some instances, these inter-sensor areas may be configured to inhibit or prevent fluid movement among different sensors, e.g., where the inter-sensor areas are coated with hydrophobic materials and/or fluid barriers, such as walls.

In certain embodiments, the substrate of the device, which may carry one or more arrays of distinct sensors, is shaped as a rectangular solid (although other shapes are possible), having a length ranging from 1 cm to 20 cm, such as 1 cm to 10 cm, including 1 cm to 5 cm; a width ranging from 0.5 cm to 10 cm, such as 1 cm to 5 cm, including 1 cm to 3 cm; and a thickness ranging from 0.1 mm to 5 mm, such as 0.5 mm to 5 mm, including 1 mm to 3 mm.

Electronic communication elements, e.g., conductive leads, may be present which are configured to electronically couple the proximity sensors to components of the system, such as processors, displays, etc. Additionally, a given proximity sensor device may include a variety of other components in addition to the proximity sensor array. Additional device components may include, but are not limited to: signal processing components, data display components (e.g., graphical user interfaces); data input and output devices, power sources, fluid handling components, wired or wireless communication components, etc.

Figure 2:
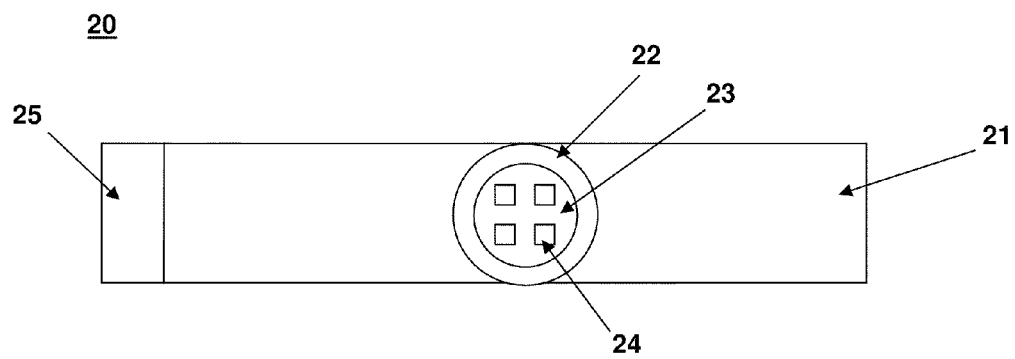
FIG. 2 shows a schematic of a device for detecting the presence of an analyte in a sample according to embodiments of the present disclosure.

An example of a device 20 for detecting the presence of an analyte in a sample according to embodiments of the present disclosure is shown in FIG. 2. The device 20 includes a substrate 21. A sample receiving member 22 is disposed on the substrate 21. The sample receiving member 22 is configured to contain a sample on the surface of the substrate 21. Although the sample receiving member 22 shown in FIG. 2 is circular in shape, other shapes are also possible, such as, but not limited to, square, elliptical, rectangular, triangular, and the like. The device also includes an array 23 of proximity sensors 24 disposed on the surface of the substrate 21. The sample receiving member 22 surrounds the array 23 of proximity sensors 24 and maintains the sample in contact with the proximity sensors 24. The array 23 may include fewer or more than the four proximity sensors 24 shown in FIG. 2. The device 20 also includes an interface 25 configured to electrically couple the device 20 to the activation and signal processing unit of the system 30 shown in FIGS. 3A and 3B.

Systems

Systems for detecting the presence of an analyte in a sample are provided. In certain embodiments, the systems include a hand-held analyte detection device, as described above. In addition, the systems include an activation and signal processing unit configured to operably couple to the hand-held analyte detection device.

Embodiments of the systems further include computer-based systems. The systems may be configured to qualitatively and/or quantitatively assess binding interactions as described above. A "computer-based system" refers to the hardware, software, and data storage components used to analyze the signals from the proximity sensors. The hardware of the computer-based systems may include a central processing unit (CPU), inputs, outputs, and data storage components. Any of a variety of computer-based system are suitable for use in the subject systems. The data storage components may include any computer readable medium that include a device for recording signals from the proximity sensors as described above, or an accessible memory component that can store signals from the proximity sensors.

To "record" data, programming or other information on a computer readable medium refers to a process for storing information, using any such methods as known in the art. Any convenient data storage structure may be chosen, depending on the method used to access the stored information. A variety of data processor programs and formats can be used for storage, e.g. word processing text file, database format, etc.

In certain embodiments, the system includes an activation and signal processing unit. The activation and signal processing unit may be configured to operably couple to the hand-held analyte detection device. In some instances, the activation and signal processing unit is electrically coupled to the analyte detection device. The activation and signal processing unit may be electrically coupled such as to provide bi-directional communication to and from the analyte detection device. For example, the activation and signal processing unit may be configured to provide power, activation signals, etc. to components of the analyte detection device, such as, but not limited to the proximity sensors. As such, the activation and signal processing unit may include an activation signal generator. The activation signal generator may be configured to provide power, activation signals, etc. to components of the analyte detection device, such as, but not limited to the proximity sensors. In some instances, the activation and signal processing unit is configured to apply a voltage across the proximity sensor ranging from 1 mV to 100 V, such as 100 mV to 50 V, including 500 mV to 10 V, for example, 500 mV to 5 V. In some cases, the activation and signal processing unit is configured to apply a voltage across the proximity sensor of 1 V.

Additionally, the activation and signal processing unit may be configured to receive signals from the analyte detection device, such as from the proximity sensors of the analyte detection device. As described above, the signals from the proximity sensors of the analyte detection device may be used to detect the presence of the analyte in the sample. In some instances, the activation and signal processing unit may include a processor configured to output an analyte detection result in response to receiving a signal from the proximity sensor. Thus, the processor of the activation and signal processing unit may be configured to receive a signal from the proximity sensor, process the signal according to a predetermined algorithm, obtain a result related to the presence of an analyte in the sample, and output the result to a user in an audible or human-readable format.

A "processor" references any hardware and/or software combination that will perform the functions required of it. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with the processor.

As discussed above, in certain embodiments, the analyte detection device includes a proximity sensor that is a magnetic sensor, and the proximity label is a magnetic label. In these embodiments, the system may include a magnetic field generator. The magnetic field generator may be positioned such that a magnetic field is produced in the area where the proximity sensors are positioned when the proximity sensor device is connected to the system. The magnetic field generator may include one or more, such as two or more, three or more, four or more magnetic field generating components. In certain embodiments, the system includes two magnetic field generators positioned on opposite sides of the proximity sensors when the proximity sensor device is connected to the system. In some cases, the magnetic field generator may include one or more electromagnets, such as a planar electromagnet. The magnetic field generator may further include a magnetic flux guide. The magnetic flux guide may be configured to direct the magnetic flux of the magnetic field generator such that the magnetic flux is substantially aligned with the direction of the hard axis of the magnetic sensors.

Figure 4:
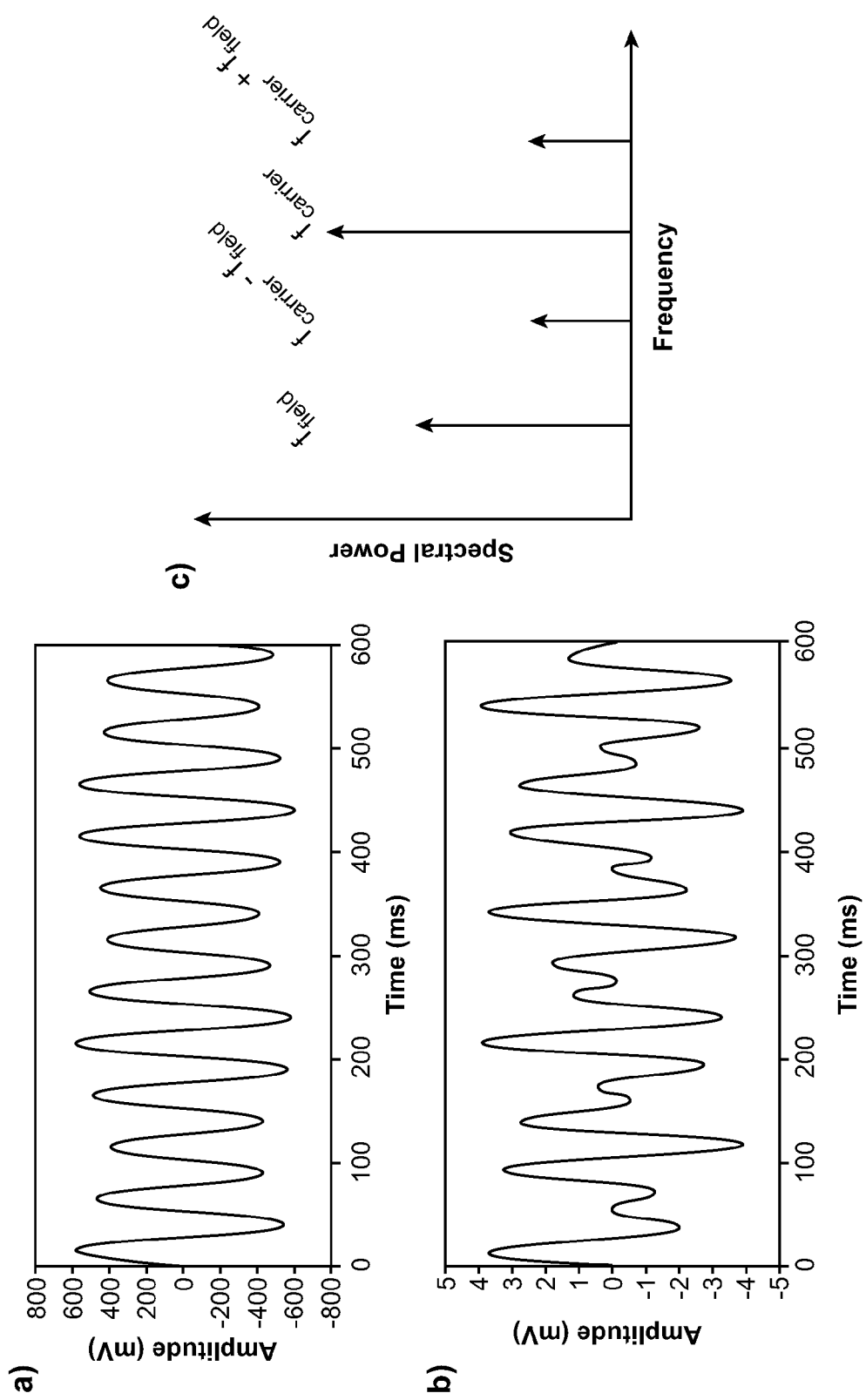
FIG. 4 shows examples of graphs of (a) the signal at the sensor, (b) the differential signal at the sensor, and (c) the spectrum of signal at the sensor showing the three distinct frequency components, as well as the electromagnetic interference at the field frequency, according to embodiments of the present disclosure.

In some instances, the subject systems are configured to modulate the current applied to the proximity sensor (e.g., the sense current). The subject systems may also be configured to modulate the magnetic field generated by the magnetic field generator. Modulating the sense current and the magnetic field may facilitate a separation of the magnetoresistive and the resistive components of the signal from the sensor and increase the signal to noise ratio. In order to detect the presence of the magnetic labels, a sense current may be applied to the proximity sensor such that changes in the resistance of the proximity sensor are converted into a detectable change in the voltage. In some instances, the signal from the sensor (see FIGS. 4(a) and 4(b)) includes other components in addition to the signal from the magnetic label, such as noise and interference between the proximity sensor and the magnetic field generators. The signal from the magnetic label may be detected by separating the signal from the magnetic label from the other components. In certain cases, a detectable signal is produced by minimizing the noise and modulating the sense current. In some instances, the signal from the sensor has a frequency, $f_{carrier}$, and the magnetic field has a frequency, $f_{field}$. In the frequency domain, modulating the sense current may shift the signal from the magnetic label to both the sum ($f_{carrier}+f_{field}$) and difference ($f_{carrier}-f_{field}$) of the sensor and magnetic field frequencies (see FIG. 4(c)). Consequently, the signal from the magnetic label and the interference between the proximity sensor and the magnetic field generators may be separated.

Modulating the current applied to the sensor and the magnetic field may also facilitate an increase in the signal to noise ratio by minimizing the noise. For example, the signal from the sensor may include noise, such as white noise, pink noise (e.g., 1/f noise), Brown noise, etc. In certain cases, the noise is due to magnetization 1/f noise, e.g., fluctuations in the magnetic field generated by the magnetic field generators, which in turn may cause fluctuations in the resistance of the magnetic sensor. Fluctuations in the resistance of the magnetic sensor may cause magnetization 1/f noise. In some instances, when the frequency of the magnetic field is low, the magnetization 1/f noise is greater than other noise components in the signal. In certain embodiments, modulating the magnetic field, such as increasing the frequency of the magnetic field, facilitates a reduction in the magnetization 1/f noise, such that the signal to noise ratio is increased.

Embodiments of the subject systems may also include the following components: (a) a wired or wireless communications module configured to transfer information between the system and one or more users, e.g., via a user computer, as described below; and (b) a processor for performing one or more tasks involved in the qualitative and/or quantitative analysis of the signals from the proximity sensors.

In certain embodiments, a computer program product is described comprising a computer usable medium having control logic (computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the proximity sensor device and activation and signal processing unit, the systems may include a number of additional components, such as, but not limited to: data output devices, e.g., monitors, speakers; data input devices, e.g., interface ports, buttons, switches, keyboards, etc.; fluid handling components; power sources; power amplifiers; wired or wireless communication components; etc. For example, the systems may include fluid handling components, such as microfluidic fluid handling components. In certain embodiments, the microfluidic fluid handling components are configured to deliver a fluid to the sample receiving member of the device, such that the fluid contacts the proximity sensors. In some cases, the fluid includes one or more of the following: an assay composition, a sample, a proximity label, a capture probe, a reagent, and the like. In certain instances, the microfluidic fluid handling components are configured to deliver small volumes of fluid, such as 1 mL or less, such as 500 μL or less, including 100 μL or less, for example 50 μL or less, or 25 μL or less, or 10 μL or less.

In certain embodiments, the system is a high-sensitivity analyte detector. By "high-sensitivity" is meant that the system is configured to detect an analyte in a sample, where the concentration of the analyte in the sample is low. In some cases, the systems are configured to produce a detectable signal indicating the presence of an analyte of interest in the sample where the concentration of the analyte in the sample is 1 μM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less.

In certain embodiments, the systems include a display. The display may be configured to provide a visual indication of an analyte detection result obtained from the activation and signal processing unit, as described above. The display may be configured to display a qualitative analyte detection result. For instance, the qualitative display may be configured to display qualitative indicators to a user that a sample includes or does not include a specific analyte of interest.

In other embodiments, the display may be configured to display an analyte detection result, where the analyte detection result is a quantitative result, e.g., a quantitative measurement of the concentration of an analyte in a sample. For example, in embodiments where the system is configured to output a quantitative analyte detection result, the system may include a display configured to display the quantitative analyte detection result. In certain instances, the quantitative analyte detection result may correspond to quantitative indicators correlated different ranges of concentrations of analyte in the sample, such as a low, medium or high amount of analyte in the sample. For example, the quantitative display may be configured such that a "low" amount of analyte corresponds to an analyte concentration ranging from 50 fM to 10 pM, a "medium" amount of analyte corresponds to an analyte concentration ranging from 10 pM to 100 pM, and a "high" amount of analyte corresponds to an analyte concentration of 100 pM to 10 nM or more. In certain embodiments, the quantitative display includes an alphanumeric display configured to display the quantitative indicators, or different colored lights (e.g., LED's, OLED's, etc.) or different symbols that each correspond to a different quantitative indicator. For example, the quantitative display may include a green light that corresponds to a low amount of analyte in the sample, an orange light that corresponds to a medium amount of analyte in the sample, and a red light that corresponds to a high amount of analyte in the sample.

In some cases, the different colored lights may be included in a single quantitative indicator, such as, but not limited to, a multi-colored (e.g., tri-colored) LED.

Figure 3A:
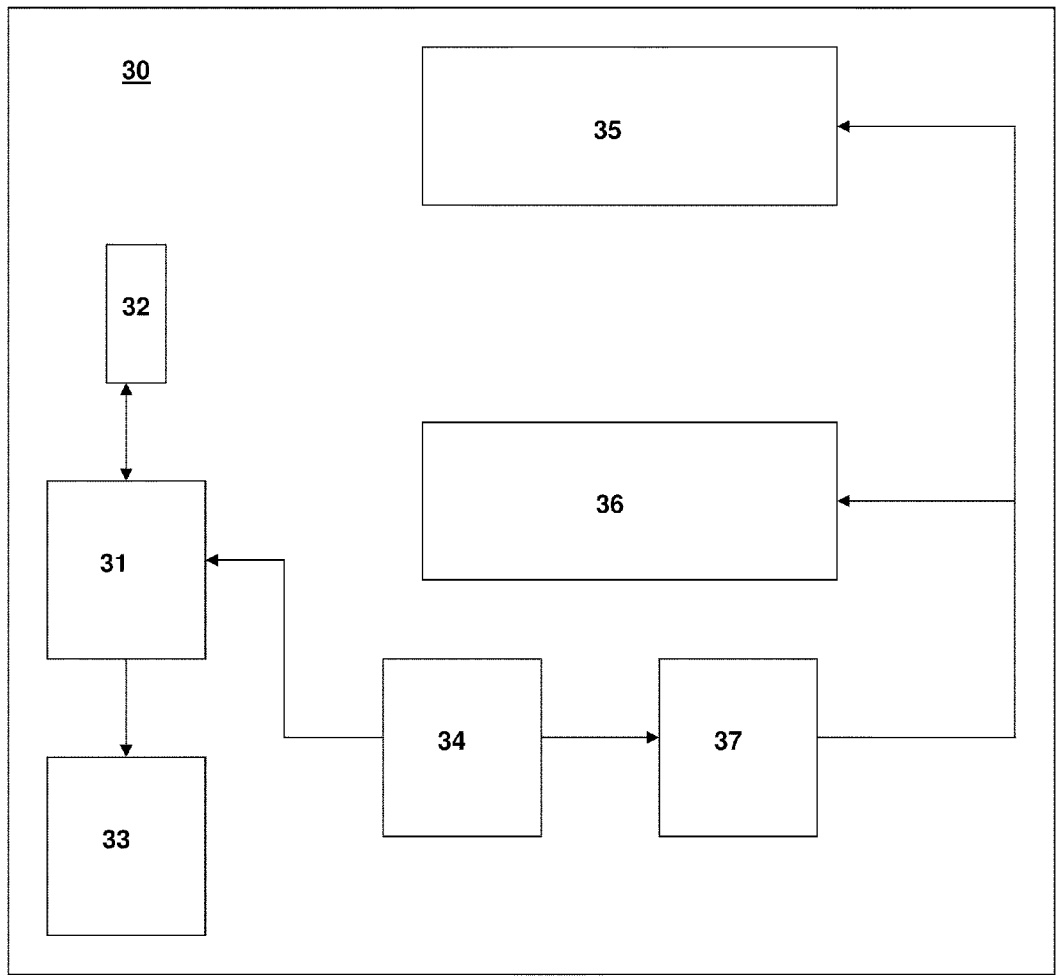
FIG. 3A shows a schematic of a system for detecting the presence of an analyte in a sample according to embodiments of the present disclosure.
Figure 3B:
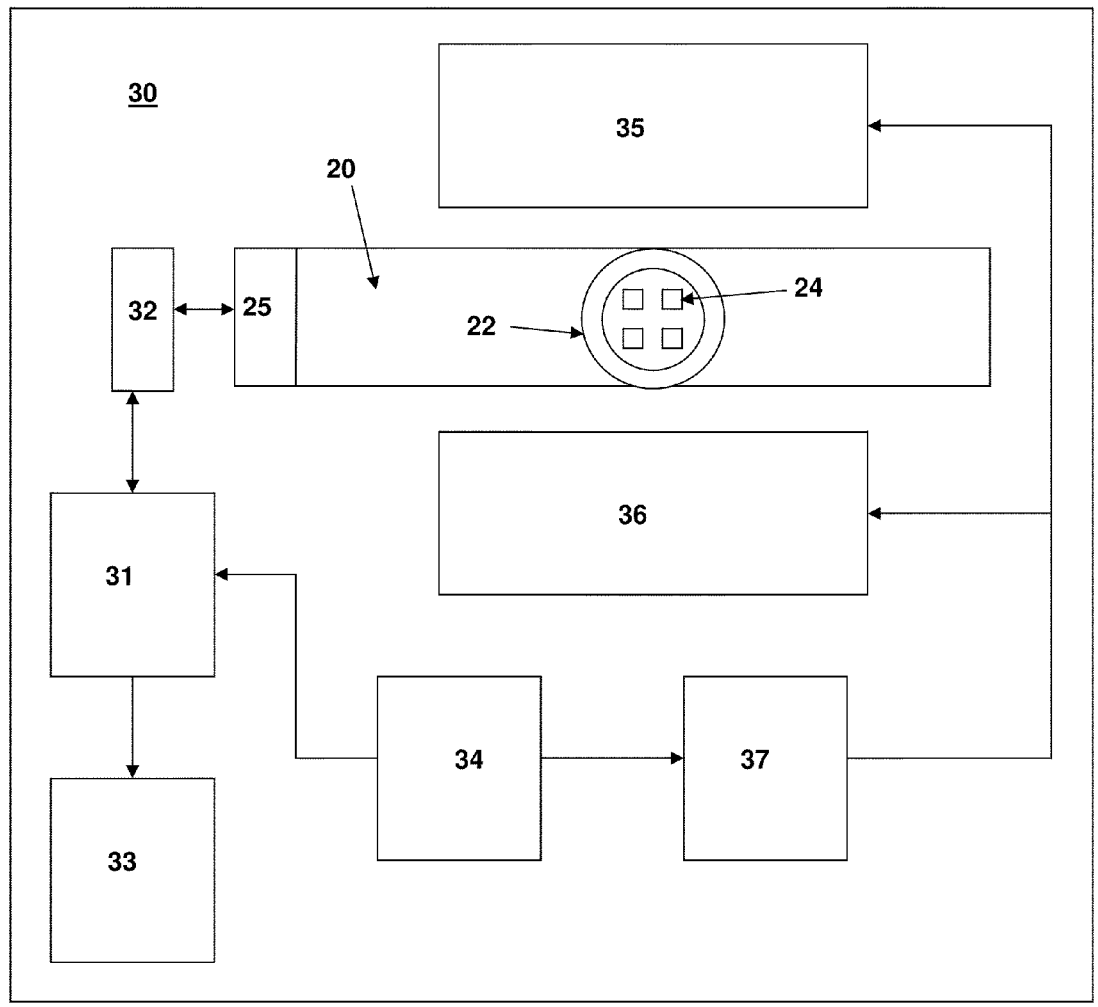
FIG. 3B shows a schematic of a device positioned in a system for detecting the presence of an analyte in a sample according to embodiments of the present disclosure.

An example of a system 30 for detecting the presence of an analyte in a sample is shown in FIGS. 3A and 3B. The system 30 includes and activation and signal processing unit 31, which is configured to operably couple to the analyte detection device 20 through interface 32. The activation and signal processing unit 31 is also operably coupled to display 33, which is configured to provide a visual indication of an analyte detection result obtained from the activation and signal processing unit 31. The system 30 also includes a power supply 34, which provides power to the activation and signal processing unit 31. The power supply 34 also provides power to the magnets 35 and 36 through power amplifier 37. As shown in FIG. 3B, to perform an assay on a sample, the analyte detection device 20 is positioned between magnets 35 and 36. The interface 25 of the analyte detection device 20 is operably coupled to the interface 32 of the system 30. The analyte detection device 20 provides a current to the proximity sensors 24. If an analyte of interest is bound to the surface of a proximity sensor 24, as described above, a signal will be induced in the proximity sensor 24. The signal will be detected and processed by the activation and signal processing unit 31 and an analyte detection result will be displayed to a user on display 33. To provide for the correct alignment of the device 20 and magnets 35 and 36 of the system 30, any convenient alignment mechanism may be employed, e.g., posts on the system 30 which insert into alignment holes in device 20 or vice versa, or other convenient alignment protocols.

Utility

The subject methods, systems and kits find use in a variety of different applications where determination of the presence or absence, and/or quantification of one or more analytes in a sample is desired. In certain embodiments, the methods are directed to detection of a set of biomarkers, e.g., two or more distinct protein biomarkers, in a sample. For example, the methods of invention may be used in the rapid, clinical detection of two or more disease biomarkers in a serum sample, e.g., as may be employed in the diagnosis of a disease condition in a subject, in the ongoing management or treatment of a disease condition in a subject, etc.

In certain embodiments, the subject methods, systems and kits find use in detecting biomarkers. In some cases, the subject methods, systems and kits may be used to detect the presence or absence of particular biomarkers, as well as an increase or decrease in the concentration of particular biomarkers in blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime.

Thus, personalized diagnosis and treatment based on the particular biomarkers or panel of biomarkers detected in an individual are facilitated by the subject methods and systems. Furthermore, the early detection of biomarkers associated with diseases is facilitated by the picomolar and/or femtomolar sensitivity of the subject methods and systems. Due to the capability of detecting multiple biomarkers on a single chip, combined with sensitivity, scalability, and ease of use, the presently disclosed assay methods and systems finds use in portable and point-of-care or near-patient multiplexed molecular diagnostics.

In certain embodiments, the subject methods, systems and kits find use in detecting biomarkers for a disease or disease state. In some cases, the disease is a cellular proliferative disease, such as but not limited to, a cancer, a tumor, a papilloma, a sarcoma, or a carcinoma, and the like. Thus, the subject methods, systems and kits find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include, but are not limited to the following: C-reactive protein, which is an indicator of inflammation; transcription factors, such as p53, which facilitates cell cycle and apoptosis control; polyamine concentration, which is an indicator of actinic keratosis and squamous cell carcinoma; proliferating cell nuclear antigen (PCNA), which is a cell cycle related protein expressed in the nucleus of cells that are in the proliferative growth phase; growth factors, such as IGF-I; growth factor binding proteins, such as IGFBP-3; micro-RNAs, which are single-stranded RNA molecules of about 21-23 nucleotides in length that regulate gene expression; carbohydrate antigen CA19.9, which is a pancreatic and colon cancer biomarker; prostate specific membrane antigen, which is a prostate cancer biomarker; cyclin-dependent kinases; epithelial growth factor (EGF); vascular endothelial growth factor (VEGF); protein tyrosine kinases; overexpression of estrogen receptor (ER) and progesterone receptor (PR); and the like.

In certain embodiments, the subject methods, systems and kits find use in detecting biomarkers for an infectious disease or disease state. In some cases, the biomarkers can be molecular biomarkers, such as but not limited to proteins, nucleic acids, carbohydrates, small molecules, and the like. For example, the subject methods, systems and kits may be used to monitor HIV viral load and patient CD4 count for HIV/AIDS diagnosis and/or therapy monitoring by functionalizing the sensor surface with antibodies to HIV capsid protein p24, glycoprotiens 120 and 41, CD4+ cells, and the like. Particular diseases or disease states that may be detected by the subject methods, systems and kits include, but are not limited to, bacterial infections, viral infections, increased or decreased gene expression, chromosomal abnormalities (e.g. deletions or insertions), and the like. For example, the subject methods, systems and kits can be used to detect gastrointestinal infections, such as but not limited to, aseptic meningitis, botulism, cholera, *E. coli* infection, hand-foot-mouth disease, *helicobacter* infection, hemorrhagic conjunctivitis, herpangina, myocaditis, paratyphoid fever, polio, shigellosis, typhoid fever, *vibrio septicemia*, viral diarrhea, etc. In addition, the subject methods, systems and kits can be used to detect respiratory infections, such as but not limited to, adenovirus infection, atypical pneumonia, avian influenza, swine influenza, bubonic plague, diphtheria, influenza, measles, meningococcal meningitis, mumps, parainfluenza, pertussis (i.e., whooping cough), pneumonia, pneumonic plague, respiratory syncytial virus infection, rubella, scarlet fever, septicemic plague, severe acute respiratory syndrome (SARS), tuberculosis, etc. In addition, the subject methods, systems and kits can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject methods, systems and kits can be used to detect urogenital diseases, such as but not limited to, AIDS, chancroid, *Chlamydia*, condyloma accuminata, genital herpes, gonorrhea, lymphogranuloma venereum, non-gonococcal urethritis, syphilis, etc. In addition, the subject methods, systems and kits can be used to detect viral hepatitis diseases, such as but not limited to, hepatitis A, hepatitis B, hepatitis C, hepatitis D, hepatitis E, etc. In addition, the subject methods, systems and kits can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject methods, systems and kits can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject methods, systems and kits can be used to detect arbovirus infections, such as but not limited to, Dengue hemorrhagic fever, Japanese encephalitis, tick-borne encephalitis, West Nile fever, Yellow fever, etc. In addition, the subject methods, systems and kits can be used to detect antibiotics-resistance infections, such as but not limited to, *Acinetobacter baumannii*, *Candida albicans*, Enterococci sp., *Klebsiella pneumoniae*, *Pseudomonas aeruginosa, Staphylococcus aureus*, etc. In addition, the subject methods, systems and kits can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc.

Similarly, the subject methods, systems and kits can be used to detect cardiovascular diseases, central nervous diseases, kidney failures, diabetes, autoimmune diseases, and many other diseases.

In certain embodiments, the subject methods, systems and kits can be used to detect the presence or absence, and/or quantification of one or more analytes in a sample for food and/or environmental safety. For example, the subject methods, systems and kits can be used to determine the presence of analytes in samples of potentially contaminated water, soil or food, such as for the detection of infectious disease agents, e.g., bacteria, viruses, molds, etc., including potential biological warfare agents.

In some instances, the subject methods, systems and kits can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Computer Related Embodiments

A variety of computer-related embodiments are also provided. Specifically, the data analysis methods described in the previous sections may be performed using a computer. Accordingly, provided is a computer-based system for analyzing data produced using the above methods in order to provide qualitative and/or quantitative determination of a binding interaction of interest.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, DVD-ROM, BD-ROM, a hard disk drive, a ROM or integrated circuit, a magneto-optical disk, a solid state memory device, a computer readable card such as a PCMCIA card, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media does not include electronic signals in transit via a wireless protocol.

With respect to computer readable media, "permanent memory" refers to memory that is permanent. Permanent memory is not erased by termination of the electrical supply to a computer or processor. Computer hard-drive, CD-ROM, DVD-ROM, BD-ROM, and floppy disk are all examples of permanent memory. Random Access Memory (RAM) is an example of non-permanent memory. A file in permanent memory may be editable and re-writable.

Kits

Also provided are kits for practicing one or more embodiments of the above-described methods. The subject kits may vary, and may include various devices and reagents. Reagents and devices include those mentioned herein with respect to proximity sensor devices or components thereof (such as a proximity sensor array or chip), proximity labels, capture probes, surface capture ligands, buffers, etc. The reagents, proximity labels, capture probes, etc. may be provided in separate containers, such that the reagents proximity labels, capture probes, etc. may be used individually as desired. Alternatively, one or more reagents, proximity labels, capture probes, etc. may be provided in the same container such that the one or more reagents, proximity labels, capture probes, etc. are provided to a user pre-combined.

In certain embodiments, the kits include a hand-held analyte detection device, as described herein, and a proximity label. In addition, the kits may include a capture probe configured to bind to the proximity label and the analyte. The kits may also include a system for detecting the presence of an analyte in a sample. As such, the kits may include an activation and signal processing unit configured to operably couple to the hand-held analyte detection device. In some instances, the hand-held analyte detection device is disposable. By "disposable" is meant that the hand-held analyte detection device is configured to be used once and then discarded. An unused hand-held analyte detection device is used for a subsequent assay. As such, the subject kits may include one or more, such as two or more, four or more, six or more, eight or more, 10 or more, etc. hand-held analyte detection devices.

In some instances, the kits include at least reagents finding use in the methods (e.g., as described above); and a computer readable medium having a computer program stored thereon, wherein the computer program, when loaded into a computer, operates the computer to qualitatively and/or quantitatively determine a binding interaction of interest from a real-time signal obtained from a proximity sensor; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, etc., on which the information has been recorded. Yet another means that may be present is a website address which may be used via the Internet to access the information at a removed site. Any convenient means may be present in the kits.

The following examples are offered by way of illustration and not by way of limitation.

EXPERIMENTAL

Proximity Sensor Array Fabrication

On silicon wafers with 150 µm thermal oxide, a spin valve film with a layer sequence similar to that of hard disk drives read heads was patterned by ion milling into individual sensors, each consisting of 32 linear segments of 1.5 µm×100 µm connected in series and arranged to cover an area of 100 µm×100 µm. Each sensor had a nominal resistance of 40 kΩ and a maximum magnetoresistance of 12%. Corrosion resistant leads (Ta 5/Au 300/Ta 5) nm were sputter deposited and patterned by liftoff. The sensors were passivated with a tri-layer oxide ($SiO_2$ 10/$Si_3N_4$ 10/$SiO_2$ 10) nm which was deposited at room temperature by ion beam sputter deposition. The leads were passivated with an additional tri-layer oxide ($SiO_2$ 100/$Si_3N_4$ 100/$SiO_2$ 100) nm. A two-component epoxy (EP5340, Eager Plastics, Chicago, Ill.) was used to assemble the chip and reagent well (Tygon® tubing, ¼" ID×⅜" OD, 6 mm long) on the ceramic 84-pin chip carrier (LCC08423, Spectrum Semiconductor Materials, San Jose, Calif.). A 0.5 mm layer of the same epoxy was used to mask some of the sensors, so as to create two adjacent but separate sites for subsequent biofunctionalization. The masked sensors, no longer able to detect proximity label binding, served as electrical signal references.

Figure 11:
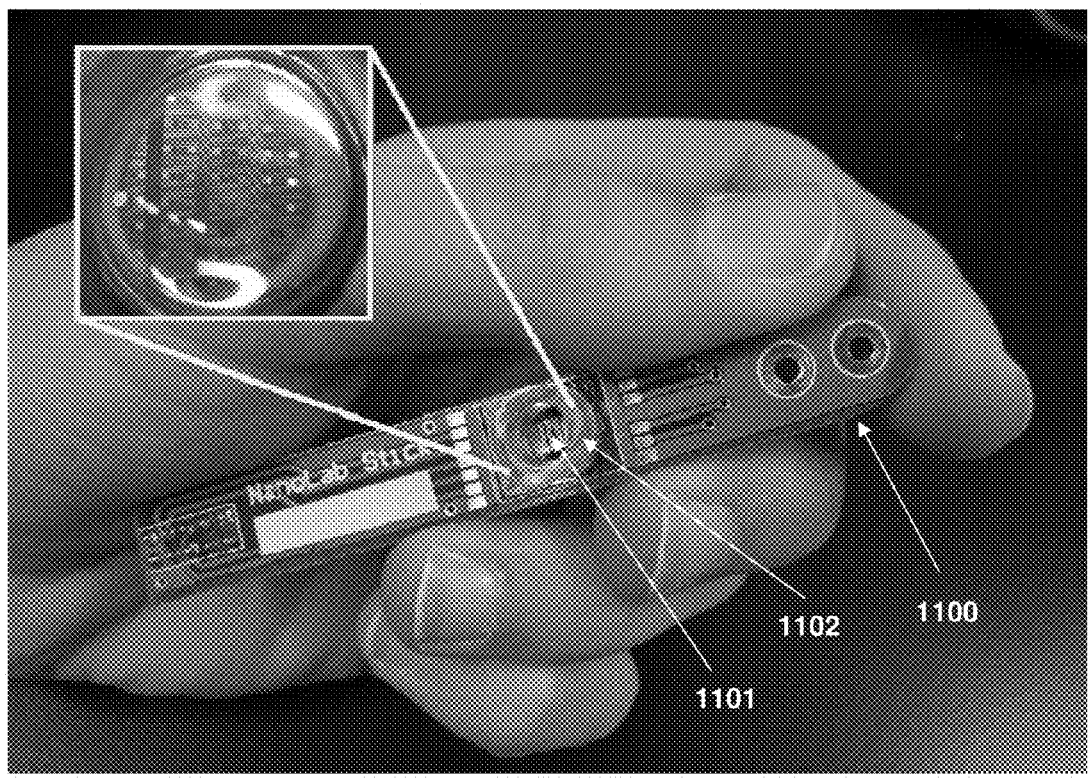
FIG. 11 shows a photograph of a hand-held device for detecting the presence of an analyte in a sample according to embodiments of the present disclosure. An enlargement of an array of proximity sensors is shown in the inset.

FIG. 11 shows a photograph of a hand-held device 1100 for detecting the presence of an analyte in a sample according to embodiments of the present disclosure. The device 1100 includes a proximity sensor array 1101 and a sample receiving member 1102 configured to contain a sample on the surface of the proximity sensor array 1101. An enlargement of the proximity sensor array 1101 is shown in the inset.

Surface Preparation

The assembled proximity sensor arrays were thoroughly washed with acetone, methanol, isopropanol, and de-ionized water. A ten minute UV ozone treatment (UVO Cleaner Model 42, Jelight, Irvine, Calif.) was used to remove organic residues. To form the base layer of the biofunctionalization, a 2% solution of polyethyleneimine (PEI, CAS 9002-98-6, Sigma-Aldrich) in deionized water was applied to the surface of the proximity sensors for 2 minutes. The proximity sensors were then rinsed with deionized water and then baked at 150° C. for 5 minutes to solidify the adsorbed PEI.

Electronics

Figure 12:
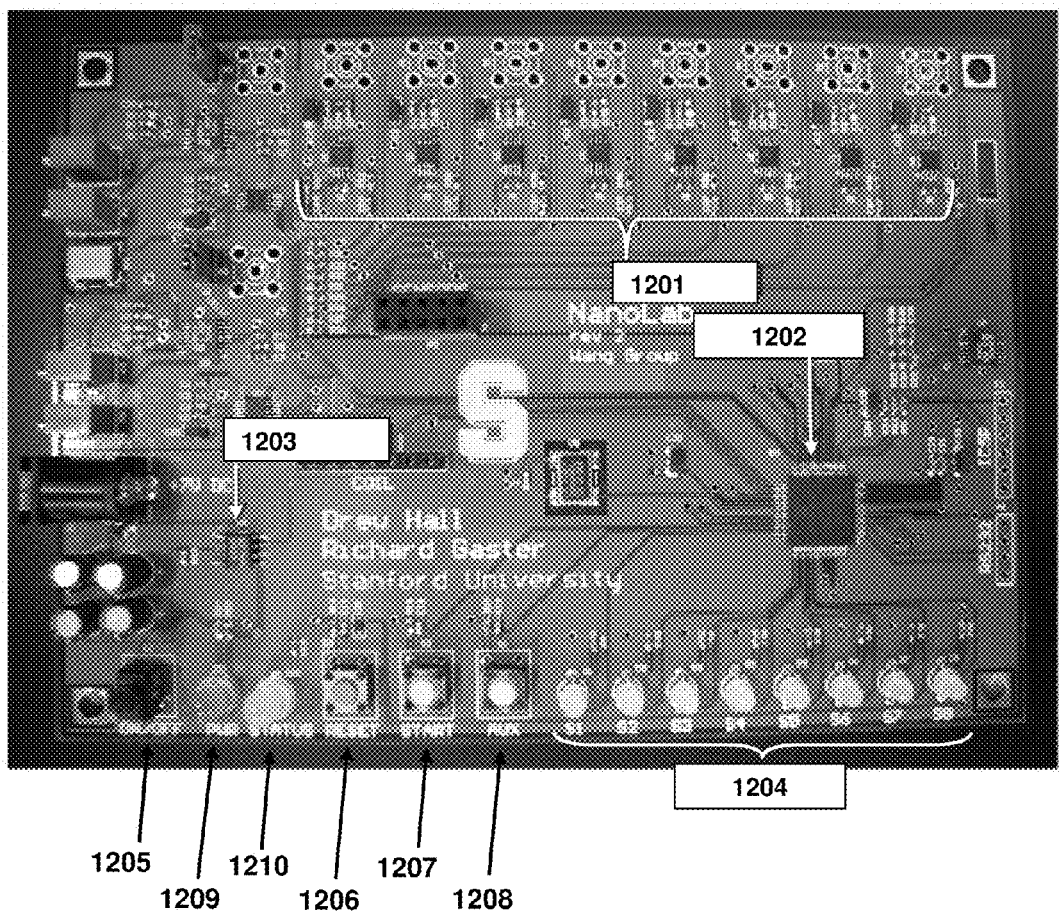
FIG. 12 shows a photograph of a data acquisition board (DAQ) according to embodiments of the present disclosure.

The electronics for the system are described as follows and shown in FIGS. 12-14. FIG. 12 shows a photograph of a data acquisition (DAQ) board 1200 according to embodiments of the present disclosure. The DAQ board 1200 had both analog and digital subcircuits. The analog circuits included the excitation signal generation and the field signal generation subcircuits. In addition, the DAQ board 1200 included the front end 1201. In addition, the DAQ board 1200 included a power supply 1203. Also included on the DAQ board 1200 was a microprocessor 1202 which performed the digital signal processing (DSP) and handled all of the user interactions.

Figure 13:
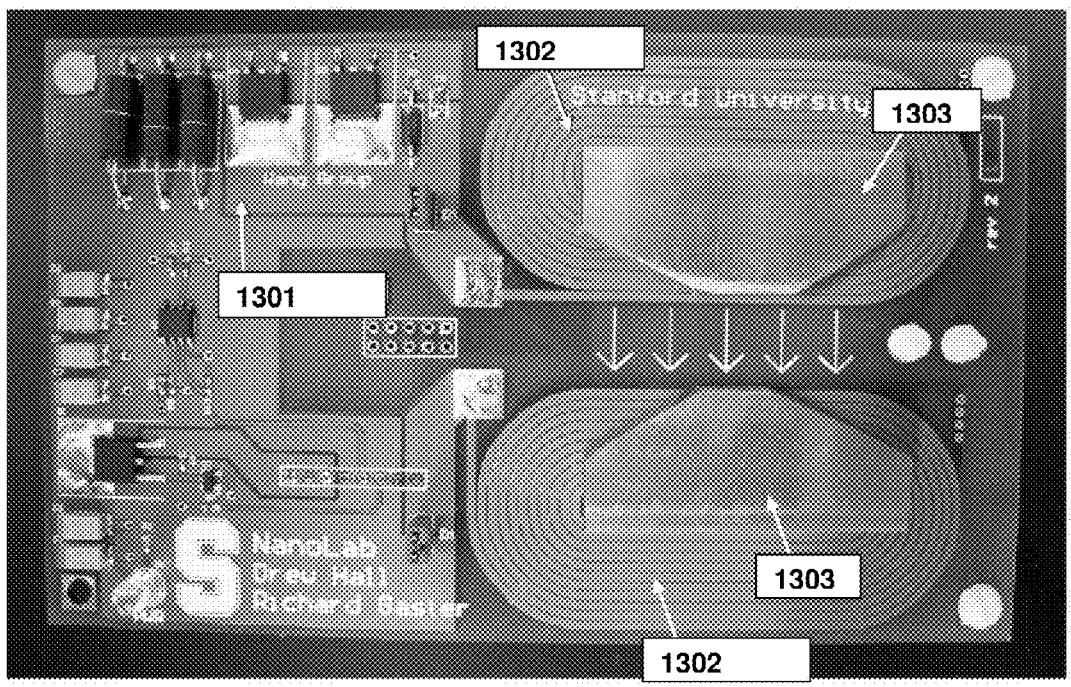
FIG. 13 shows a photograph of an electromagnetic coil board according to embodiments of the present disclosure.

FIG. 13 shows a photograph of an electromagnetic coil board 1300 according to embodiments of the present disclosure. The electromagnetic coil board 1300 contained a power amplifier 1301 and planar electromagnets 1302 used to generate the magnetic field to modulate the sensors. The electromagnetic coil board also included magnetic flux guides 1303.

Figure 14:
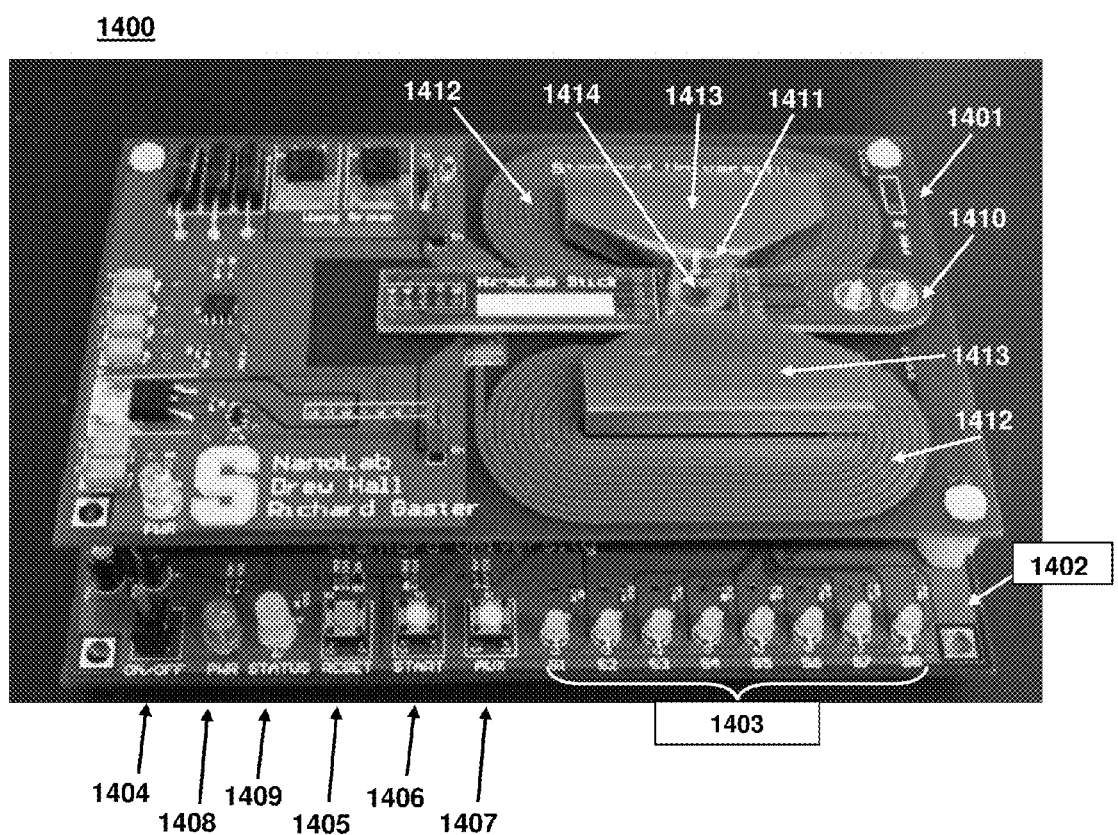
FIG. 14 shows a photograph of a system for detecting the presence of an analyte in a sample according to embodiments of the present disclosure.

FIG. 14 shows a photograph of a system 1400 for detecting the presence of an analyte in a sample according to embodiments of the present disclosure. The system included an electromagnetic coil board 1401 connected to a data acquisition (DAQ) board 1402. The DAQ board 1402 included LED indicators 1403 configured to display a quantitative analyte detection result. In addition, the DAQ board 1402 included several buttons (e.g., an on/off button 1404, a reset button 1405, a start button 1406, and an auxiliary button 1407) and LEDs (e.g., a power LED 1408, a status LED 1409, and LED indicators 1403). The system 1400 also included a disposable hand-held analyte detection device 1410 configured to detect the presence of an analyte in a sample. The disposable hand-held analyte detection device 1410 included a proximity sensor array 1414 (e.g., a GMR sensor array) mounted on a printed circuit board (PCB), and did not include any other electronics (e.g., a magnetic field generator). The disposable hand-held analyte detection device 1410 included a sample receiving member 1411. The sample receiving member 1411 surrounded the proximity sensor array 1414 and was configured to contain a sample in contact with the proximity sensor array 1414. The sample receiving member 1411 and proximity sensor array 1414 were positioned between the planar electromagnets 1412 and magnetic flux guides 1413.

Figure 5:
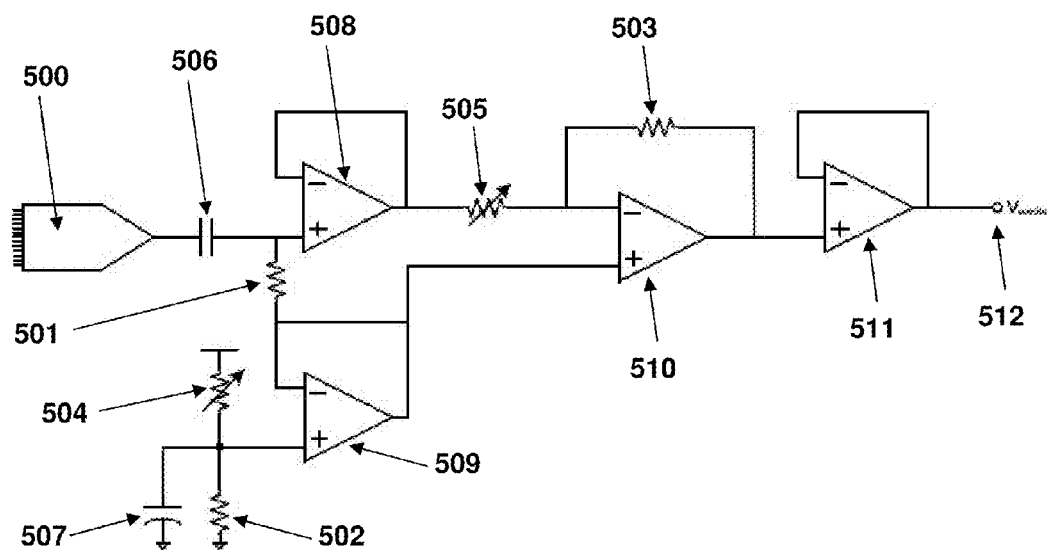
FIG. 5 shows a schematic of circuitry used to generate the excitation signal for the proximity sensors and the excitation signal for the magnetic field generators, according to embodiments of the present disclosure.

FIG. 5 shows a schematic of a portion of the circuitry that was used to generate and condition the excitation signal for the sensors. The sensors were excited by a sinusoidal signal with a peak amplitude of 0.5 V and an offset of 1 V. A direct digital synthesis (DDS) chip 500 with a 10-bit digital to analog converter (DAC) was used to synthesize the signal. The subsequent signal conditioning circuits level-shifted the output and applied gain. The signal was buffered before driving the sensors. An identical circuit also generated the signal that was used to drive the electromagnetic coil. The excitation signal for the electromagnetic coil was also sinusoidal but had a peak amplitude of 660 mV and an offset of 360 mV. The circuitry shown in FIG. 5 included resistors 501, 502 and 503, and adjustable resistors 504 and 505. The circuitry also included capacitors 506 and 507. In addition, the circuitry included amplifiers 508, 509, 510, and 511. The circuitry schematic in FIG. 5 also shows voltage output 512, which was configured to output the excitation signal, $V_{excite}$, to the sensors (see FIG. 6).

Figure 6:
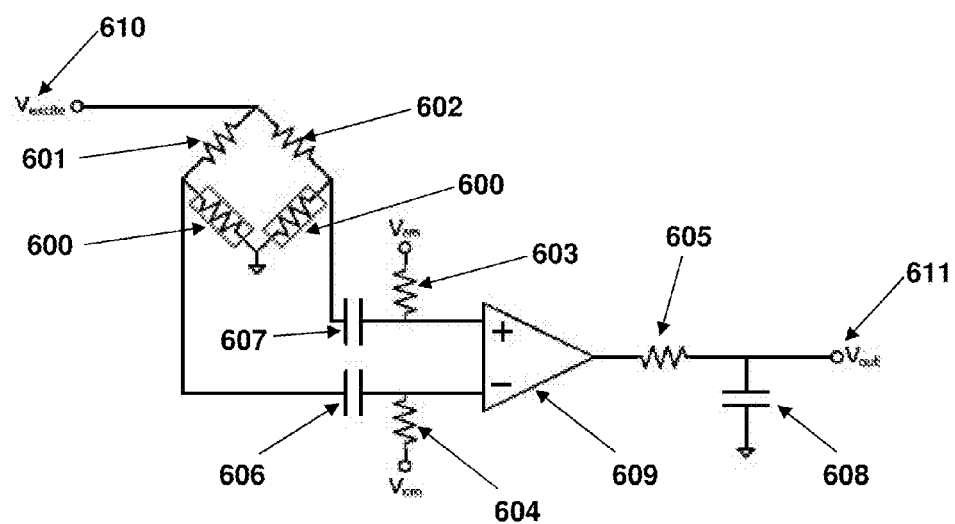
FIG. 6 shows a circuitry schematic of the analog front-end for each proximity sensor according to embodiments of the present disclosure.

The front-end for the sensor (FIG. 6) included a classical Wheatstone bridge with a high gain instrumentation amplifier. The proximity sensors were the resistors 600 shown in FIG. 6. The reference sensor in the Wheatstone bridge (e.g., left half of the bridge) was shared among all eight sensors. The signal from the Wheatstone bridge contained a large common mode with a small differential component (see FIGS. 4(a) and 4(b)). In order to remove the sensor-sensor variation (DC offset) the signals were high pass filtered (HPF). After filtering, the common mode voltage of the signals was adjusted to be in the high gain region for the instrumentation amplifier. A low pass anti-aliasing filter (AAF) was used before the signals were digitized by the analog to digital converter (ADC) inside of the microprocessor. Each of the sensors included a circuit as shown in FIG. 6. The circuitry shown in FIG. 6 also included resistors 601 and 602 as part of the Wheatstone bridge. In addition, the circuitry included resistors 603, 604 and 605, and capacitors 606, 607 and 608. Amplifier 609 is also shown in the circuitry schematic in FIG. 6. The circuitry schematic also shows voltage input 610, which is configured to input the excitation signal, $V_{excite}$, from the sensor excitation circuitry shown in FIG. 5. The circuitry schematic in FIG. 6 also shows voltage output 611, which is configured to output the signal, $V_{out}$, from the sensor to the activation and signal processing unit of the system.

Figure 7:
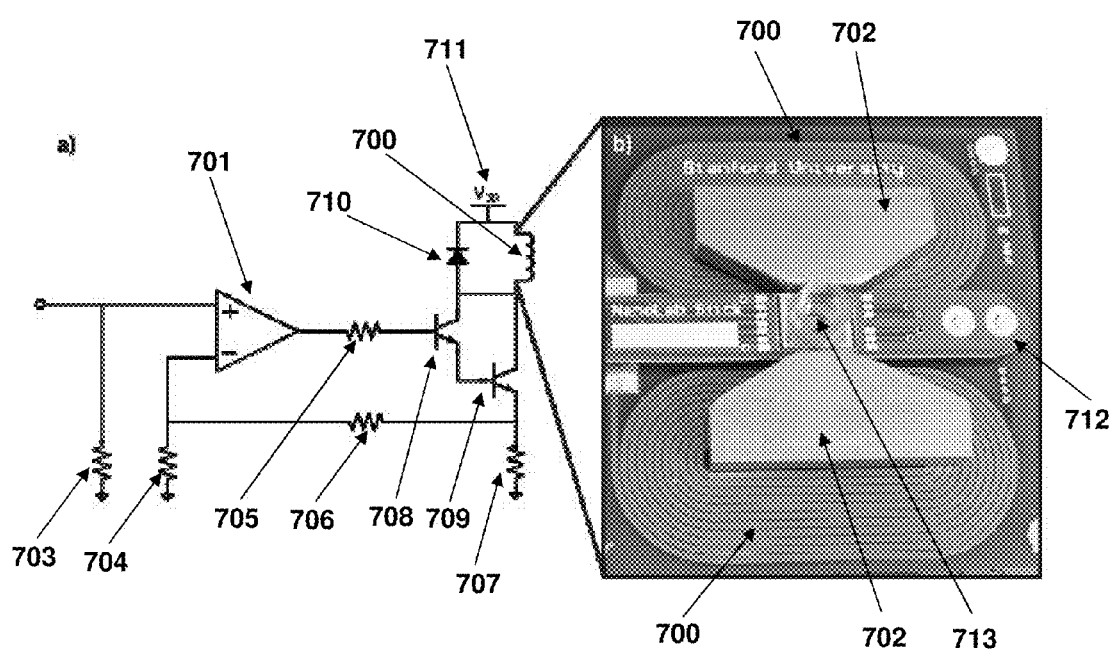
FIG. 7($a$) shows a circuitry schematic for an electromagnetic coil driver according to embodiments of the present disclosure.

FIG. 7(a) shows a circuitry schematic for an electromagnetic coil driver according to embodiments of the present disclosure. The electromagnetic coil driver included resistors, 703, 704, 705, 706, and 707. In addition, the electromagnetic coil driver included transistors 708 and 709, and diode 710. The electromagnetic coil driver also included power supply 711. The coil board contained planar electromagnet coils 700, which were made out of traces on a four layer circuit board (see FIG. 7(b)). In order to generate a large enough magnetic field to excite the sensor, a substantial amount of current needed to be provided to the coil. To handle this current, a power amplifier 701 was used. The planar electromagnet coils 700 were largely inductive, 400 μH, with a resistive component of 4.5Ω. A soft magnetic material was attached to the surface of the planar electromagnet coils 700 to act as magnetic flux guides 702. The magnetic flux guides 702 were configured to direct the magnetic flux to be oriented in the direction of the hard axis of the GMR sensors. A device 712 for detecting the presence of an analyte in a sample is shown with its proximity sensor array 713 positioned between the planar electromagnetic coils 700 and magnetic flux guides 702.

The signals were digitized and processed by a microprocessor 1202 (Microchip dsPIC30F6012A, Microchip Technology, Inc., Chandler, Ariz.), as shown on FIG. 12. The microprocessor 1202 applied a high order digital filter to isolate out the side tone from all of the interfering signals (the excitation tone, the coupled magnetic field, and other noise). Once the side tone was separated, the root mean square (RMS) of the signal was calculated. This value was displayed to the user by colored light emitting diode (LED) indicators 1204. Each proximity sensor in the proximity sensor array has a corresponding LED indicator 1204. The LED indicators 1204 are tri-colored LEDs that emit a green light corresponding to a low amount of analyte in the sample, an orange light corresponding to a medium amount of analyte in the sample, and a red light corresponding to a high amount of analyte in the sample. In addition to the signal processing, the microprocessor 1202 also performed housekeeping work, such as initializing the DDS chips, turning on and off the electromagnet to save power, and handling the user interface which included several buttons (e.g., an on/off button 1205, a reset button 1206, a start button 1207, and an auxiliary button 1208) and LEDs (e.g., a power LED 1209, a status LED 1210, and LED indicators 1204).

Results

Figure 8:
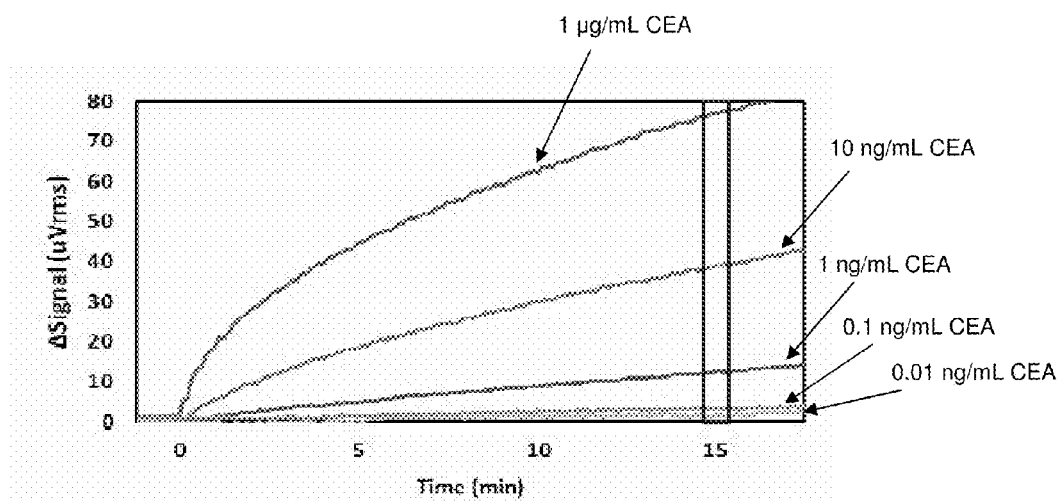
FIG. 8 shows a graph of superimposed real-time binding curves of capture probe (which in some embodiments may be a detection antibody, e.g., in the context of sandwich ELISA assays) to captured antigen using a protein detection assay according to embodiments of the present disclosure. Concentrations of carcinoembryonic antigen (CEA) ranging from 1 μg/mL (5 nM) to 10 pg/mL (50 fM) were tested and shown to be detectable above background. The assay was run for 15 minutes, therefore, the signal observed at 15 minutes (indicated in the box at 15 min) was used to generate the calibration curve.

In order to translate sensor signals into a useable output, a calibration curve was first generated. Using the calibration curve, it was possible to obtain protein detection by converting the measured signal from unknown samples into distinct regions on the curve. Real-time binding curves were monitored over a range of protein concentrations (FIG. 8). FIG. 8 shows real-time binding curves of detection antibody to various concentrations of carcinoembryonic antigen (CEA), a known colorectal cancer tumor marker.

Figure 9:
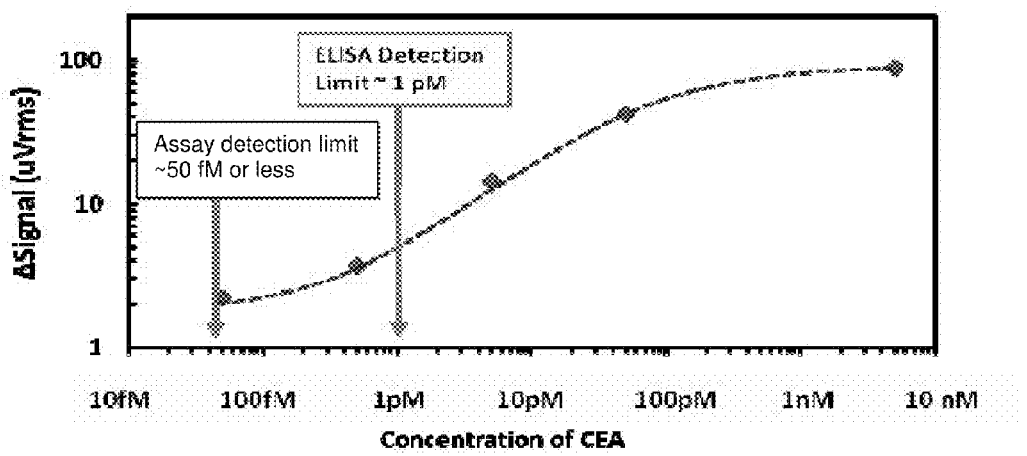
FIG. 9 shows a graph of a calibration curve of the assay according to embodiments of the present disclosure. The lower limit of quantifiable protein detection in the assay was approximately 50 fM.

The assay was run for 15 minutes to allow sufficient time for the signals to rise while still being rapid enough for point-of-care utility. To generate the calibration curve, the signals obtained at 15 minutes were plotted as a function of protein concentration (FIG. 9). It was observed that the lower limit of detection was about 50 fM, which is over an order of magnitude more sensitive than ELISA.

Figure 10:
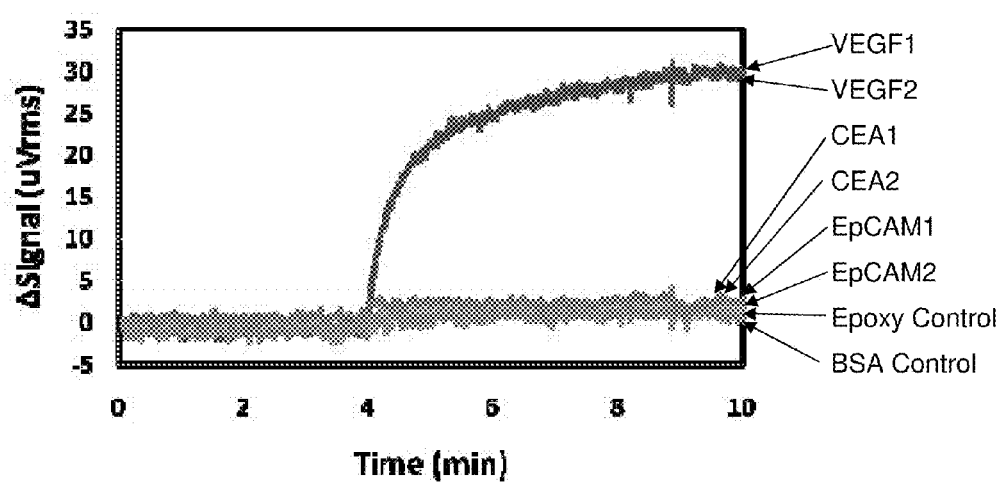
FIG. 10 shows a graph of binding of vasculoendothelial growth factor (VEGF), CEA, and epithelial cell adhesion molecule (EpCAM) to sensors with surface capture ligands specific to VEGF only, according to embodiments of the present disclosure. Sensors coated with epoxy and bovine serum albumin (BSA) were used as negative controls.

In order to show the specificity, multiplexing capacity, and reproducibility of the assay, protein detection of vasculoendothelial growth factor (VEGF), CEA and epithelial cell adhesion molecule (EpCAM) was monitored on duplicate sensors (FIG. 10). Two negative controls, an epoxy coated control and a bovine serum albumin (BSA) control, were also monitored in a single assay. After incubating the sensors with surface capture ligands specific to VEGF only, both sensors monitoring VEGF gave reproducible protein detection signals. In addition, the non-complementary antibodies to CEA and EpCAM both gave negligible signals indicating the high specificity of the reaction. The BSA control also remained flat, which showed the minimal non-specific binding of the assay. The epoxy control also remained flat indicating that there was negligible noise contribution from the electronics.

The signals from each sensor were displayed to the user through colored LEDs. Inside of the microprocessor, several tables were programmed that contained calibration curves for each protein of interest as well as the corresponding threshold concentrations (e.g., undetectable, low, medium, and high). The signal value at 15 minutes of incubation time was compared to the predetermined thresholds and the appropriate color was selected and displayed for each LED. Since 8 sensors were monitored in a single assay, the conversion from a signal input to a color light output was repeated eight times for each of the indicators on the system. The tables were pre-programmed into the system prior to use allowing the user to determine rough quantitative detection of analytes of interest in a sample by observing the color of the indicator.

Antibody Cross-Reactivity Assay
GMR Sensor Chip Fabrication and Surface Chemistry A spin valve film with a layer sequence similar to that of hard disk drives read heads was patterned by ion milling into individual sensors on a 150 μm thermal oxide in a silicon wafer. The GMR spin valve sensor array was fabricated according to Osterfeld, S. J. et al. *Proceedings of the National Academy of Sciences*, 105, 20637-40 (2008). After fabrication, the GMR sensor surface was first cleaned with acetone, methanol and isopropanol and dried with nitrogen air. Organic materials were removed by exposing the chips to oxygen plasma (PDC-32G Basic Plasma Cleaner, Harrick Plasma, Ithaca, N.Y.) for 10 minutes. Subsequently, a 2% solution of polyethylenimine (PEI, CAS 9002-98-6, Sigma Aldrich) in deionized water was added to the chip. After 3 minutes incubation, the chips were rinsed with deionized water and then baked for 15 minutes at 150° C. Next, a piezoelectric non-contact spotter (Scienion sciFlexarrayer, BioDot, Irvine, Calif.) was employed to deposit 3×360 picoliter droplets of surface capture ligand (total volume of 1 nanoliter). Anti-EGFR, anti-CEA, anti-EpCAM, anti-Trop2, anti-beta 2 microglobulin, anti-survivin, anti-PRDX6, anti-serpin, anti-HE4, anti-AGR2, anti-CA125, anti-TNF-alpha, anti-Insulin, anti-GCSF, anti-Lactoferrin, anti-VTCN, anti-SLPI, anti-mesothelin and anti-Eotaxin were each placed over at least three sensors at a concentration of 100 μg/mL to 1 mg/mL. In addition, control sensors were covered with 1% bovine serum albumin (BSA) in phosphate buffered saline (PBS). A group of reference sensors were also deposited with a two component epoxy. The surface capture ligands were incubated for 1 hour at room temperature at 90% relative humidity. The reaction well was subsequently washed with a washing buffer (0.1% BSA and 0.5% Tween 20 in PBS) and then blocked with 50 μL of 1% BSA in PBS for 30 minutes.

After addition of analyte to the reaction well, no washing steps were required. For some of the experiments presented, washing steps were initially performed in order to minimize the complexity of the reaction taking place, however, the assay performed as well when no wash was performed.

Magnetic Proximity Label

The magnetic proximity labels were purchased commercially from Miltenyi Biotech Inc. The magnetic proximity labels included about a dozen 10 nm iron oxide nanoparticles embedded in a dextran polymer with 10% magnetic material (wt/wt). The surface of the magnetic proximity label was functionalized with streptavidin. The entire magnetic proximity label was approximately 50 nm in diameter, the zeta potential was −11 mV, and the translational diffusion coefficient was $8.56 \times 10^{-12}$ $m^2$ $s^{-1}$. The magnetic proximity labels were colloidally stable, such that they did not settle non-specifically on the sensor surface.

Antibody Cross-Reactivity Assay Protocol

20 μL of sample was added to the reaction well containing a solution of the analyte of interest at 10 ng/mL. The following proteins were tested: EGFR, beta 2 microglobulin, survivin, PRDX6, EpCAM, CEA, Serpin, HE4, AGR2, CA125, Trop2, TNF-alpha, Insulin, GCSF, Lactoferrin, VTCN, SLPI, Mesothelin, Eotaxin, and BSA. After 5 minutes incubation, the sample was washed away with a washing buffer (0.1% BSA and 0.05% Tween 20 in PBS) and 20 μL of magnetic proximity labels, functionalized with streptavidin (MACS 130-048-102, Miltenyi Biotec, Auburn, Calif.), were added to the reaction well. 10 μL of each biotinylated capture probe complementary to the target analyte of interest at a concentration of 10 μg/mL was introduced sequentially. Upon introduction of each capture probe, the solution was immediately pipetted up and down 10 times to insure rapid and thorough mixing in the reaction well. The GMR sensors were monitored in real-time for antibody cross-reactivity.

Example 1

Figure 15:
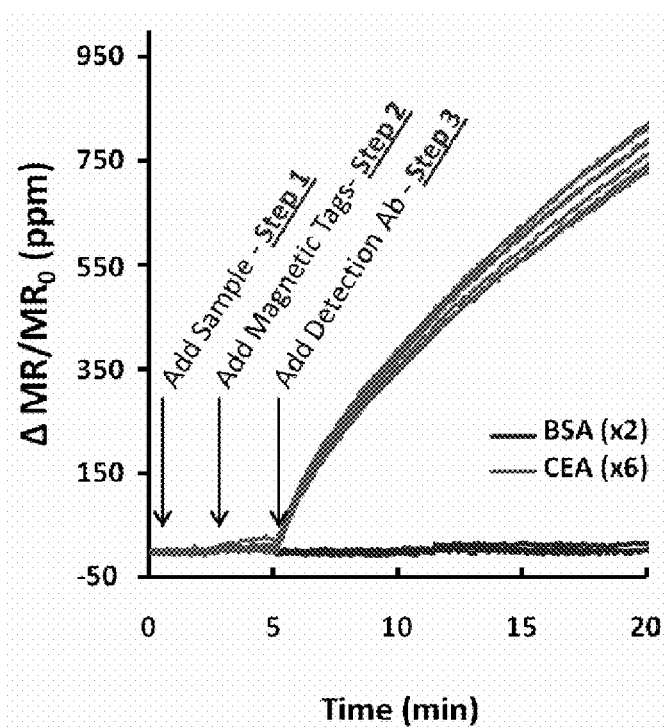
FIG. 15 shows a graph of real-time monitoring of proximity sensors according to embodiments of the present disclosure. The y-axis units are the change in magnetoresistance normalized to the initial magnetoresistance presented in parts per million (ppm).

The cross-reactivity of an anti-epidermal growth factor receptor (EGFR) antibody to a panel of 20 unique target proteins was examined. After selectively capturing each protein via antibody surface capture ligands, magnetic proximity labels were added. The GMR signal was monitored in real time. There was no significant rise in the GMR signal upon addition of sample and magnetic proximity labels (FIG. 15). The biotinylated anti-EGFR capture probes were added next. Once the capture probes were introduced, the magnetic proximity labels were bound to the sensor surface within the detection range of the proximity sensor and in high enough density to be detected by the underlying GMR sensor (FIG. 15). Each sensor in the array was individually addressable and monitored in real-time. Therefore, upon sequential addition of different capture probes at different time points, it was possible to determine the specific antibody capture probe that was cross-reacting in a panel of antibodies. The negative control sensors were coated with bovine serum albumin (BSA) and the signal from the negative control sensors remained flat, indicating negligible non-specific binding.

Figure 16A:
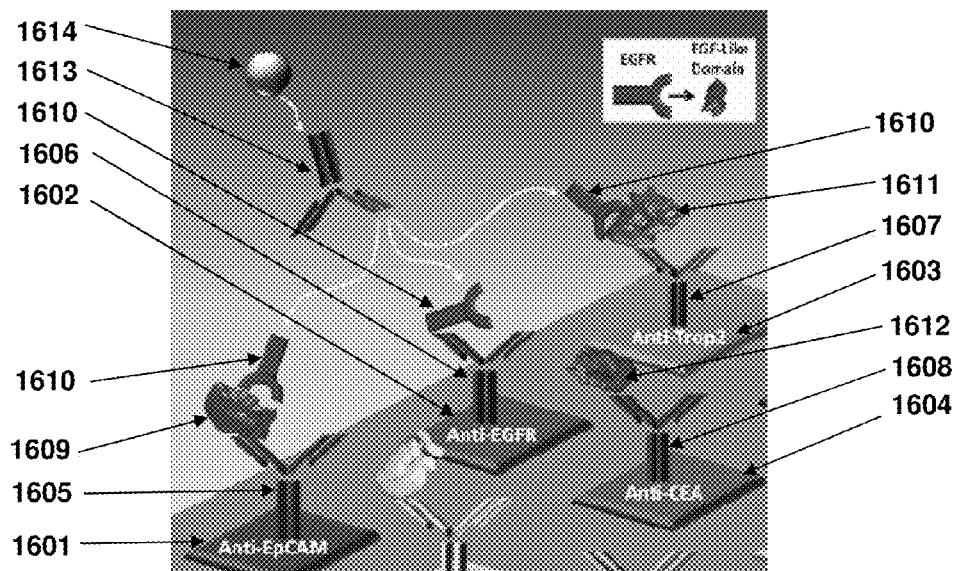
FIG. 16($a$) shows an illustration of an antibody cross-reactivity assay according to embodiments of the present disclosure.
FIG. 16(c) shows a graph of an antibody cross-reactivity assay where anti-EGFR capture probe was introduced first and exhibited cross-reactivity with EpCAM-bound sensor.
FIG. 16(d) shows another graph of an antibody cross-reactivity assay where anti-Trop2 capture probe was introduced first and exhibited cross-reactivity with EFGR-bound sensor.
Figure 16B:
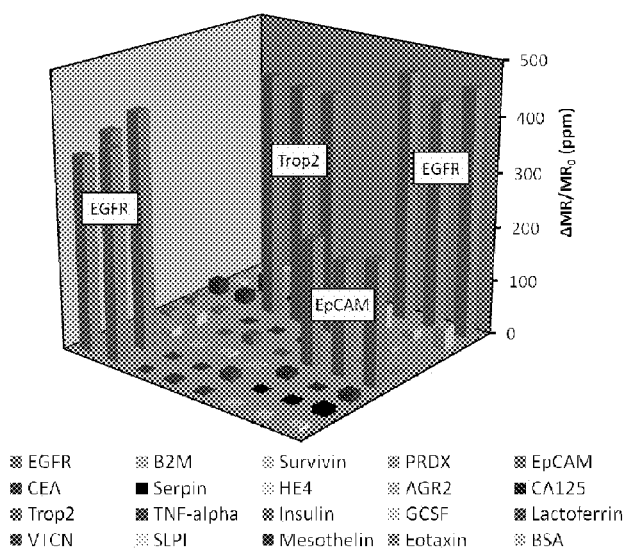

While the majority of proteins showed no detectable cross-reaction, the assay was able to detect two proteins in addition to EGFR that were bound by the anti-EGFR antibody; the epithelial cell adhesion molecule (EpCAM) and human trophoblast cell-surface antigen (Trop2 also termed GA733-1, M1S1, or EGP-1) (FIGS. 16(a) and 16(b)). FIG. 16(a) shows an illustration of the antibody cross-reactivity assay. Proximity sensors 1601, 1602, 1603 and 1604 each had different surface capture ligands 1605, 1606, 1607 and 1608 bound to the sensor surface. For example, proximity sensor 1601 had anti-EpCAM surface capture ligand 1605 bound to its surface; proximity sensor 1602 had anti-EGFR surface capture ligand 1606 bound to its surface; proximity sensor 1603 had anti-Trop2 surface capture ligand 1607 bound to its surface; and proximity sensor 1604 had anti-CEA surface capture ligand 1608 bound to its surface. FIG. 16(a) also shows analytes bound to the surface capture ligands. For example, FIG. 16(a) shows Ep-CAM 1609 bound to the anti-EpCAM surface capture ligand 1605; EGFR 1610 bound to the anti-EGFR surface capture ligand 1606; Trop2 1611 bound to the anti-Trop2 surface capture ligand 1607; and CEA 1612 bound to the anti-CEA surface capture ligand 1608. In addition, FIG. 16(a) shows EGFR 1610 cross-reacting and binding to EGF-like domains on Ep-CAM 1609 and Trop2 1611. Upon introduction of anti-EGFR capture probes 1613, the anti-EGFR capture probes 1613 specifically bind to EGFR 1610 that is bound to the anti-EGFR surface capture ligand 1606, and also to EGFR 1610 that is bound to the EGF-like domains on Ep-CAM 1609 and Trop2 1611. Binding of the proximity labels 1614 to the capture probes 1613 positions the proximity labels 1614 in the detection range of the proximity sensors, allowing the detection of the binding of EGFR 1610 to the anti-EGFR surface capture ligand 1606 and also the cross-reactivity of EGFR 1610 to the EGF-like domains on Ep-CAM 1609 and Trop2 1611.

Figure 16C:
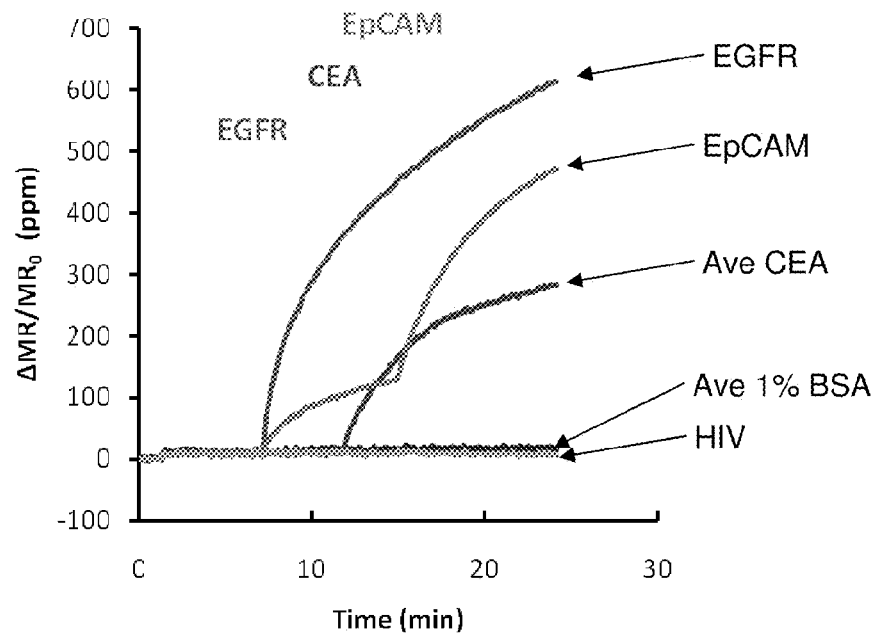

As shown in FIG. 16(c), anti-EGFR antibody capture probe was added first to the assay composition. The anti-EGFR antibody capture probe bound to the EGFR protein, as shown by the change in magnetoresistance normalized to the initial magnetoresistance presented in parts per million (ppm). In addition, the anti-EGFR antibody capture probe also bound to the EpCAM protein, as described above. Upon addition of the anti-CEA capture probe, however, no such cross-reaction was observed; only the sensor with anti-CEA surface capture ligands exhibited a binding curve. There was no detectable signal over the non-complementary antibody (e.g., HIV) and BSA control sensors, indicating no settling or nonspecific binding of the magnetic proximity labels.

Figure 16D:
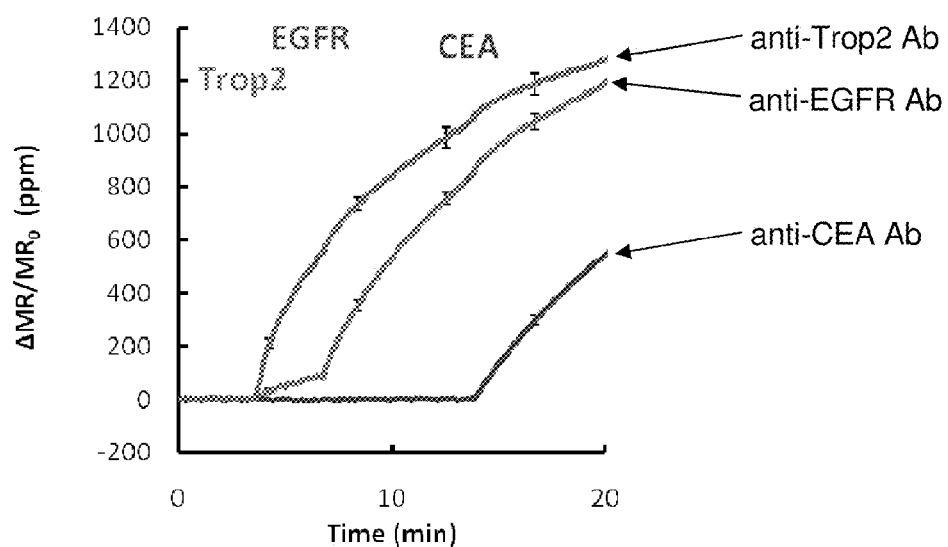

Similarly, as shown in FIG. 16(d), when anti-Trop2 capture probe was added, the anti-Trop2 capture probe not only bound to the sensor bound to Trop2 protein, but also bound to the sensor bound to EGFR protein. Anti-CEA antibody, however, again showed no cross-reaction.

Figure 20A:
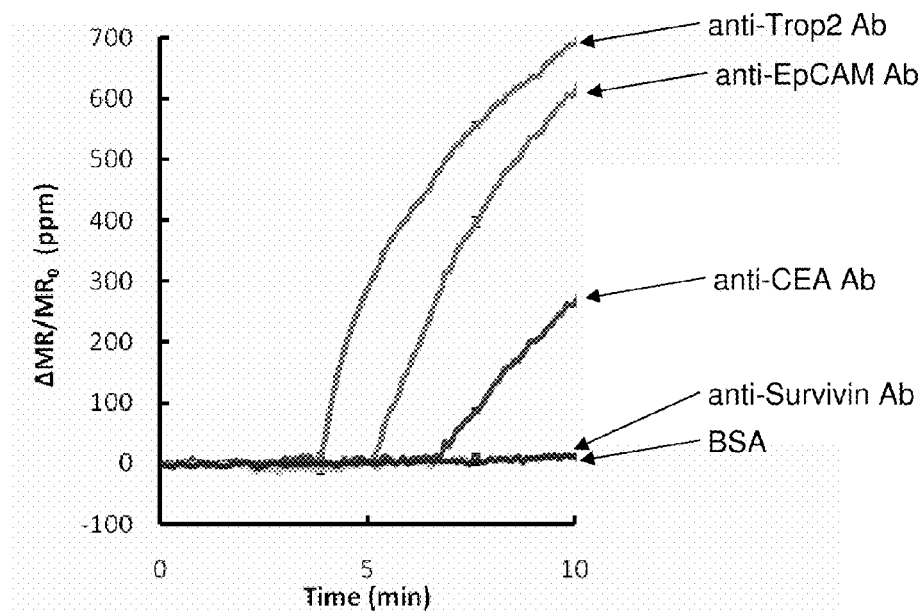
FIG. 20(a) shows a graph of a control experiment showing no cross-reactivity between anti-Trop2, anti-EpCAM and anti-CEA capture probes according to embodiments of the present disclosure.
Figure 20B:
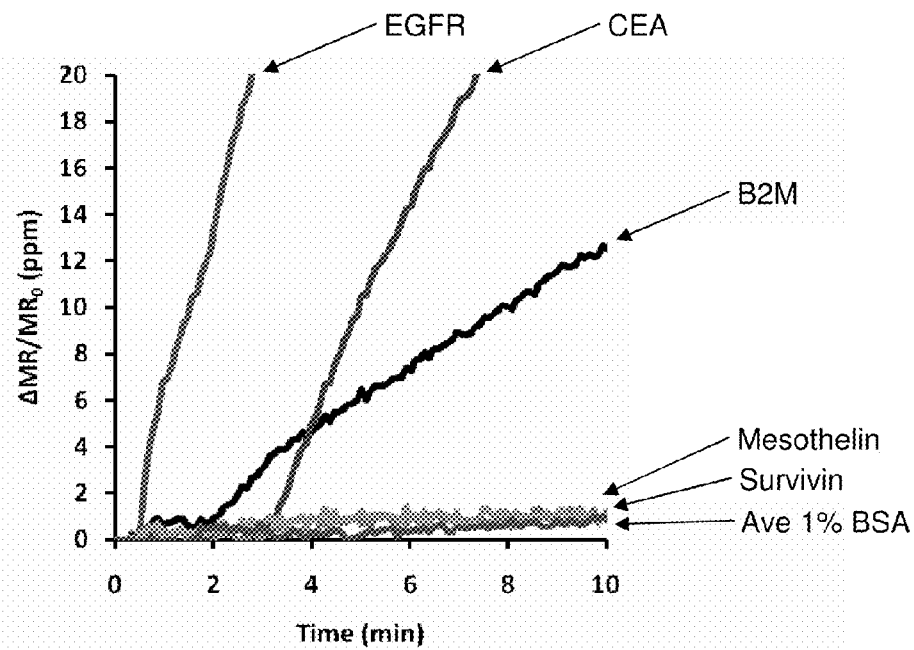
FIG. 20(b) shows a graph of a control experiment showing no cross-reactivity between anti-EGFR, anti-B2M, and anti-CEA capture probes according to embodiments of the present disclosure.

FIG. 20(a) shows a graph of a control experiment showing no cross-reactivity between anti-Trop2, anti-EpCAM and anti-CEA capture probes. Introduction of anti-Trop2 capture probe, anti-EpCAM capture probe and anti-CEA capture probe showed no cross-reaction or non-specific binding among the proteins tested. Similarly, in a separate set of experiments, introduction of anti-EGFR antibody, anti-B2M antibody and anti-CEA antibody showed no cross-reaction or non-specific binding among the proteins tested. FIG. 20(b) shows a graph of a control experiment showing no cross-reactivity between anti-EGFR, anti-B2M, and anti-CEA capture probes. In addition, the anti-EGFR antibody and anti-CEA antibody had higher binding affinities than anti-B2M antibody as shown by the more rapid rise in signal upon addition of the capture probe.

Figure 17:
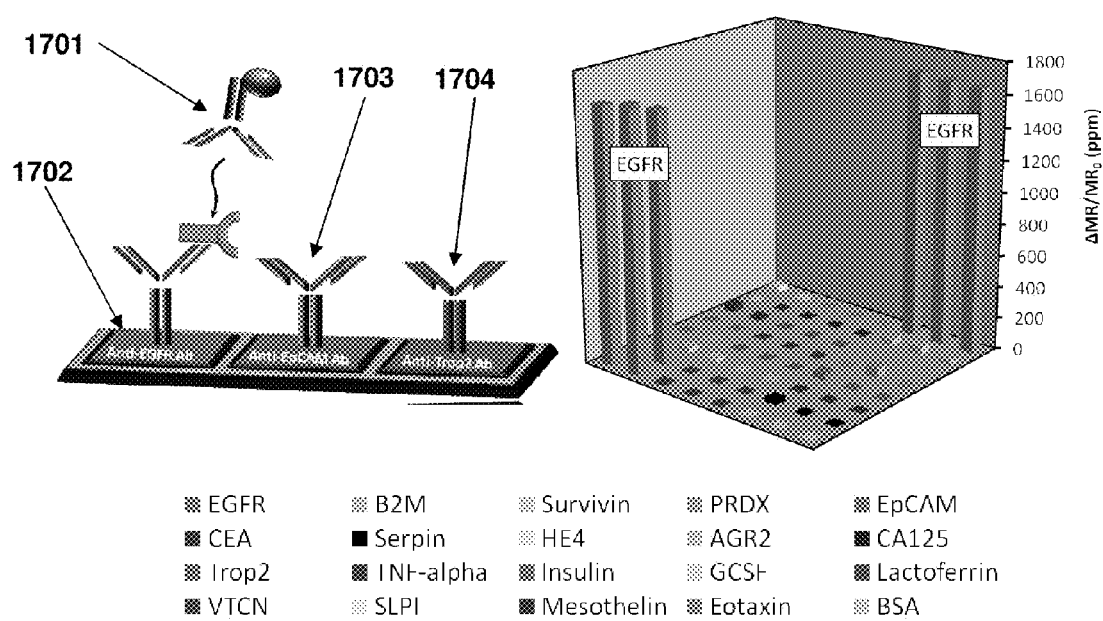
FIG. 17 shows an illustration and graph of a control experiment where EpCAM and Trop2 proteins were excluded from the assay composition according to embodiments of the present disclosure.
Figure 18:
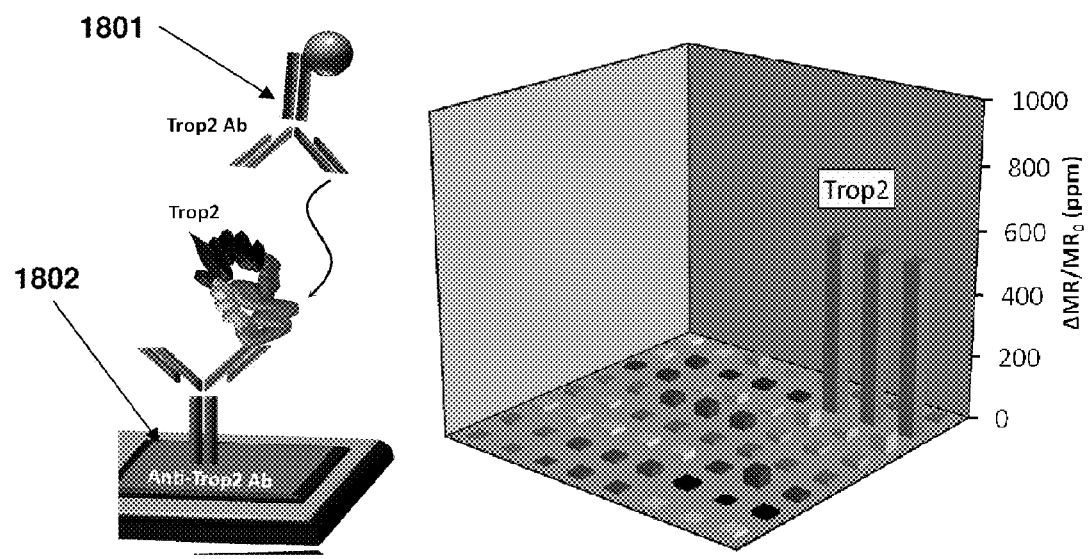
FIG. 18 shows an illustration and graph of a control experiment where EGFR protein was excluded from the assay composition according to embodiments of the present disclosure.

Control experiments, where Trop2 and EpCAM were absent (FIG. 17), and where EGFR protein was absent (FIG. 18), each showed no cross-reactivity, which confirmed that the cross-reaction was due to capture probe-analyte interaction and not due to capture probe binding to surface capture ligand (see FIGS. 17 and 18). FIG. 17 shows an illustration and graph of the control experiment where EpCAM protein and Trop2 protein were excluded from the assay composition. All other proteins listed were included. Upon addition of anti-EGFR capture probe 1701, only the EGFR sensors 1702 gave a detectable signal, which indicated that the anti-EGFR capture probe 1701 did not bind to any of the other surface capture ligands 1703 and 1704 used. The anti-EGFR capture probe 1701 only cross-reacted with the Trop2 and EpCAM proteins themselves. FIG. 18 shows an illustration and graph of a control experiment where EGFR protein was excluded from the assay composition. Similar to the control experiment shown in FIG. 17, all other proteins were included. Upon addition of anti-Trop2 capture probe 1801, only the Trop2 sensors 1802 gave a detectable signal, which indicated that the anti-Trop2 capture probe 1801 did not bind to any of the other surface capture ligands used. Thus, EGFR, which was capable of binding EGF-like domains, bound to the EGF-like domains of captured Trop2 and EpCAM protein as well as captured EGFR protein.

Figure 19:
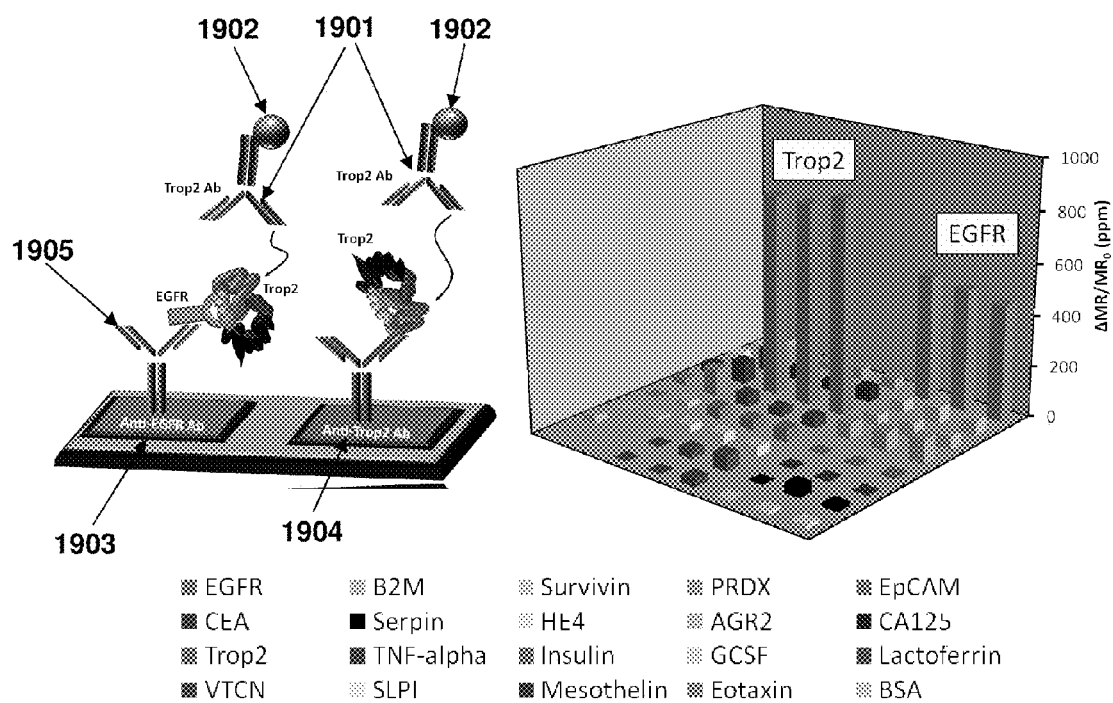
FIG. 19 shows an illustration and graph of an antibody cross-reactivity experiment according to embodiments of the present disclosure.

FIG. 19 shows an illustration and graph of an antibody cross-reactivity assay where anti-Trop2 antibody capture probes 1901 were introduced instead of anti-EGFR antibody capture probes, as described above. Twenty different surface capture ligands were each bound to different proximity sensors. All 20 proteins were incubated at a concentration of 10 ng/mL. After washing, magnetic proximity labels 1902 were added followed by anti-Trop2 capture probes 1901. The assay was run for 5 minutes resulting in signal over the EGFR sensor 1903 and Trop2 sensor 1904. Thus, cross-reactive binding between anti-Trop2 capture probes 1901 over the EGFR sensor 1903 functionalized with anti-EGFR surface capture ligands 1905 was observed. Thus, the antibody cross-reactivity assay was able to detect cross-reactivity in both directions (e.g., cross-reactivity of EGFR to the EGF-like domains on Ep-CAM and Trop2, and cross-reactivity of Trop2 to the EGFR bound to the EGFR sensor functionalized with anti-EGFR surface capture ligands). (see FIGS. 16(a), 16(b) and 19).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The subject matter claimed in this patent application was made as a result of activities undertaken within the scope of a joint research agreement between The Board of Trustees of the Leland Stanford Junior University and MagArray, Inc.

What is claimed is:

1. A method of detecting the presence of an analyte in a sample, the method comprising:
   contacting a magnetic sensor comprising a surface capture ligand that specifically binds to an analyte with an assay composition comprising a sample and a magnetic proximity label;
   introducing a capture probe into the assay composition, wherein the capture probe is configured to bind to the magnetic proximity label and the analyte to produce a labeled analyte; and
   obtaining a signal from the magnetic sensor to detect the presence of the labeled analyte in the sample,
   wherein the method is a wash-free method.

2. The method according to claim 1, wherein the method comprises producing the assay composition by sequentially contacting the sensor with the sample and the proximity label.

3. The method according to claim 1, wherein the method comprises combining the sample and the proximity label to produce the assay composition and then contacting the sensor with the assay composition.

4. The method according to claim 1, wherein the method comprises detecting the presence of two or more analytes in the sample.

5. The method according to claim 1, wherein the method comprises detecting the cross-reactivity of an analyte or antibody.

6. The method according to claim 5, wherein the detecting comprises sequentially introducing different capture probes into the assay composition, wherein each different capture probe is configured to specifically bind to a distinct analyte.

7. The method according to claim 5, further comprising detecting specific binding of each capture probe to its corresponding analyte.

8. The method according to claim 1, wherein the proximity sensor is a component of a hand-held device.

9. The method according to claim 1, wherein the presence of the analyte in the sample is detected qualitatively.

10. The method according to claim 1, wherein the presence of the analyte in the sample is detected quantitatively.

11. The method according to claim 1, wherein the proximity label is a colloidal proximity label.

12. The method according to claim 11, wherein the proximity label comprises a magnetic label and a polymer.

13. The method according to claim 12, wherein the polymer comprises dextran.

14. The method according to claim 1, wherein the capture probe is configured to non-covalently bind to the proximity label.

15. The method according to claim 14, wherein the proximity label is functionalized with a first member of a binding pair and the capture probe is functionalized with a complementary member of the binding pair.

* * * * *

UNITED STATES PATENT AND TRADEMARK OFFICE
CERTIFICATE OF CORRECTION

PATENT NO.        : 9,506,919 B2
APPLICATION NO.   : 12/759584
DATED             : November 29, 2016
INVENTOR(S)       : Gaster et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1441 days.

Signed and Sealed this
Twenty-fifth Day of September, 2018

Andrei Iancu
*Director of the United States Patent and Trademark Office*